United States Patent [19]

Mukai et al.

[11] Patent Number: 4,968,725

[45] Date of Patent: Nov. 6, 1990

[54] DENTAL ADHESIVE COMPOSITION

[75] Inventors: Nobuhiro Mukai, Nishi; Hitoshi Ige, Ohtake; Takayuki Makino, Ohtake; Junko Atarashi, Ohtake, all of Japan

[73] Assignee: Mitsubishi Rayon Co., Ltd., Tokyo, Japan

[21] Appl. No.: 221,549

[22] Filed: Jul. 20, 1988

[30] Foreign Application Priority Data

Jul. 31, 1987 [JP] Japan ................ 62-190314
Dec. 28, 1987 [JP] Japan ................ 62-335727
Jan. 6, 1988 [JP] Japan ................ 63-000816

[51] Int. Cl.$^5$ .................. C08L 75/08; C08G 18/04
[52] U.S. Cl. .................. 522/90; 522/96; 522/64; 522/171; 522/174; 528/72; 528/75
[58] Field of Search .................. 522/64, 96, 90

[56] References Cited

U.S. PATENT DOCUMENTS

| | | | |
|---|---|---|---|
| 3,759,809 | 9/1973 | Carlick et al. | 522/97 |
| 4,435,540 | 3/1984 | Kishida et al. | 524/780 |
| 4,459,193 | 7/1984 | Ratcliffe et al. | 522/96 |
| 4,539,382 | 9/1985 | Omura et al. | 522/96 |
| 4,645,649 | 2/1987 | Nagao | 422/186.3 |
| 4,657,941 | 4/1987 | Blackwell | 522/96 |
| 4,678,819 | 7/1987 | Sasaki et al. | 523/171 |

OTHER PUBLICATIONS

C. G. Roffey, Photopolymerization of Surface Coatings, 1982, p. 88.

*Primary Examiner*—Marion E. McCamish
*Assistant Examiner*—Susan Berman
*Attorney, Agent, or Firm*—Cushman, Darby & Cushman

[57] ABSTRACT

Disclosed are dental adhesive compositions consisting essentially of
 (a) at least one urethane prepolymer containing one or more isocyanate groups, or a blend of the urethane prepolymer and an inert diluent;
 (b) at least one radical-polymerizable unsaturated monomer;
 (c) a photopolymerization initiator;
and, if desired,
 (d) a polymerizable phosphoric ester compound having a specific structure.

These dental adhesive compositions can be used to bond a restorative material to dentin without requiring any troublesome pretreatment with an etching agent such as phosphoric acid, and can exhibit bonding power sufficient for practical purposes.

21 Claims, No Drawings

DENTAL ADHESIVE COMPOSITION

BACKGROUND OF THE INVENTION

1. Field of the Invention

This invention relates to dental adhesive compositions which have excellent bonding properties and are useful in bonding living dental tissues to materials (such as metals, organic polymers and ceramics) used for the restoration thereof

2. Description of the Prior Art

In the field of dental materials, a variety of materials have conventionally been used for the purpose of restoring carious teeth (also called decayed teeth) and missing teeth. Such materials include metals such as gold, silver, platinum, alloys and amalgam; organic high polymers such as polymethyl methacrylate, polycarbonate, cured products of multifunctional vinyl resins, and composite resins; and ceramic such as porcelain and implant materials. However, these materials are inherently incapable of adhering to living tooth tissues. Accordingly, in order to achieve bonding between restorative materials and living tooth tissues, there have been proposed a number of dental adhesive compositions containing, as the adhesive component, a compound having any of various polar groups (such as a phosphate group, hydroxyl group or acid anhydride group) with the intention of improving their interaction with the principal inorganic components, such as apatite (a calcium phosphate), or principal organic components, such as collagen (a protein), constituting the tooth tissues.

When the aforesaid prior art adhesive compositions are used to bond a restorative material to living tooth tissues, they have considerable adhesivity to enamel, but completely fail to exhibit adhesivity to dentin. This is due to the physical and chemical structures of living dentin. Specifically, dentin has a structure in which a vast number of dentinal tubules are penetrated and filled with a body fluid. Moreover, dentin contains a fairly high proportion of proteins such as collagen, as compared with enamel. Thus, it may be said that, from the viewpoint of bonding, dentin is in a very adverse environment. Accordingly, the aforesaid prior art adhesive compositions require pretreatment of the principal inorganic component as apatite, with an etching agent (such as phosphoric acid) so as to produce the so-called anchoring effect which brings about a certain degree of bonding to living dentin. Nevertheless, because of the insufficiency of bond strength, a gap will be produced between the restorative material and the dentin over a long time and, in the worst case, the restorative material may even fall off. Thus, the prior art adhesive compositions cannot be said to have bonding properties adequate for practical purposes.

SUMMARY OF THE INVENTION

It is an object of the present invention to provide a novel photopolymerizable dental adhesive composition which, when used to bond a restorative material to living tooth tissues, has high adhesivity to enamel and, moreover, exhibit practically sufficient adhesivity to dentin, without requiring any troublesome pretreatment with an etching agent (such as phosphoric acid) that has been indispensable in the prior art.

According to the present invention, there is provided a dental adhesive composition consisting essentially of (a) at least one urethane prepolymer containing one or more isocyanate groups, or a blend of the urethane prepolymer and an inert diluent;
(b) at least one radical-polymerizable unsaturated monomer; and
(c) a photopolymerization initiator.

According to the present invention, there is also provided another dental adhesive composition consisting essentially of (a) at least one urethane prepolymer containing one or more isocyanate groups, or a blend of the urethane prepolymer and an inert diluent;
(b) at least one radical-polymerizable unsaturated monomer;
(c) a photopolymerization initiator; and
(d) a polymerizable phosphoric ester compound of the general formula (1):

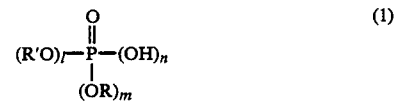

where R is a group selected from the class consisting of

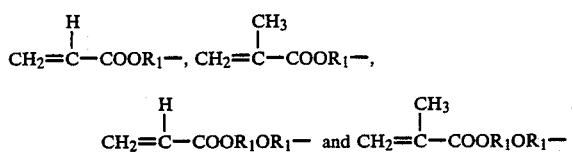

in which $R_1$ is an alkylene group, $R'$ is an alkyl group, n is 1 or 2, m is 1 or 2, l is 0 or 1, and the sum of $(n+m+l)$ is equal to 3.

DETAILED DESCRIPTION OF THE PREFERRED EMBODIMENTS

The urethane prepolymer containing one or more isocyanate groups, which is used as component (a) in the compositions of the present invention, is a compound obtained by reacting a polyol compound with a polyisocyanate [i.e., a compound having two or more isocyanate (—NCO) groups per molecule] in such a way that part of the isocyanate groups remain unreacted.

The polyol compound used for this purpose may be selected from polyether polyols and polyester polyols. Specific examples of useful polyether polyols include compounds formed by effecting addition polymerization of an alkylene oxide (such as propylene oxide or ethylene oxide) to a low-molecular-weight compound having two or more hydroxyl groups per molecule (such as glycol, glycerol, sorbitol or sucrose). Specific examples of useful polyester polyols include compounds formed by effecting polycondensation of a dibasic acid (such as adipic acid) with a glycol (such as ethylene glycol) so as to give terminal hydroxyl groups; compounds formed by reacting a hydroxyl-containing higher fatty acid (such as ricinoleic acid) with glycerol; and compounds obtained from natural sources, such as castor oil and its derivatives.

Such polyether polyols can be prepared according to the conventional method which comprises adding an alkaline catalyst (such as potassium hydroxide or sodium hydroxide) to an active hydrogen compound (such as ethylene glycol, propylene glycol or 1,6-hexanediol) and effecting addition polymerization of an alkylene oxide (such as ethylene oxide, propylene oxide or butylene oxide) to the active hydrogen compound In order to obtain excellent bonding properties, it is preferable to use a polyol compound having terminal hydroxyl groups.

By way of example, urethane prepolymers having one or more isocyanate groups can be obtained by reacting, in the presence of a conventional catalyst such as a tertiary amine or dibutyltin laurate, the above-defined polyol compound with an organic isocyanate (such as tolylene diisocyanate, 4,4'-diphenylmethane diisocyanate or hexamethylene diisocyanate) in such an NCO/OH equivalent ratio as to provide an excess of NCO.

Among these urethane prepolymers, there may preferably be used urethane prepolymers of the following structural formulas (2), (3) and (4) which are derived from a diol obtained by using propylene glycol as an active hydrogen compound and effecting addition polymerization of ethylene oxide and propylene oxide to it. In particular, urethane prepolymers obtained by using tolylene diisocyanate, 4,4'-diphenylmethane diisocyanate or hexamethylene diisocyanate as a terminal isocyanating agent and containing at least two free isocyanate group per molecule are preferred because of their exceptionally high adhesivity. More specifically, urethane prepolymers containing free isocyanate groups at both ends are especially preferred.

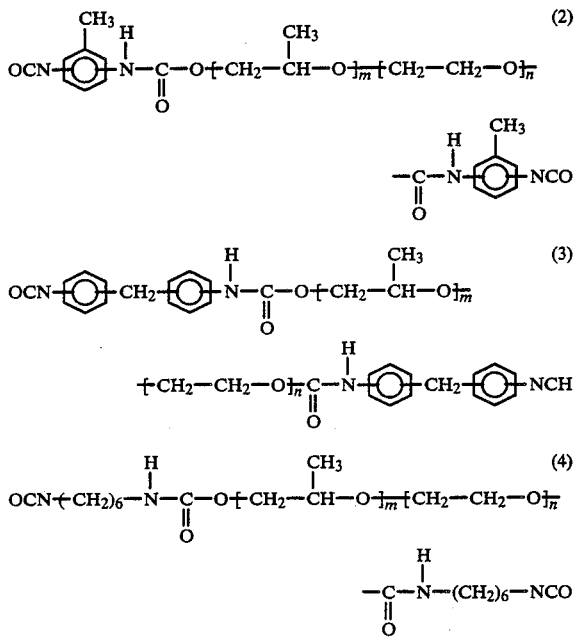

In the above formulas, m is a whole number of 1 to 100, n is a whole number of 0 to 100, and the propylene oxide units may be randomly joined to the ethylene oxide units.

These urethane prepolymers preferably have a molecular weight of 400 to 50,000 and more preferably 400 to 20,000, chiefly for the purpose of obtaining good solubility in radical-polymerizable unsaturated monomers, as well as excellent bonding properties.

With regard to the isocyanate-containing urethane prepolymers of formulas (2) to (4) it is preferable that they be rendered hydrophilic or watersoluble by adjusting their ethylene oxide unit content to a level of 40 to 80 mole percent based on the combined amount of the propylene oxide units and ethylene oxide units constituting the prepolymer chain.

On the other hand, the dibasic acids constituting polyester polyols useful for the aforesaid purpose include adipic acid, azelaic acid, sebacic acid, maleic acid, phthalic acid, isophthalic acid or terephthalic acid. The polyols constituting such polyester polyols include ethylene glycol, propylene glycol, 1,4-butanediol, 1,6-hexanediol, diethylene glycol, neopentyl glycol, glycerol, trimethylolpropane or pentaerythritol.

Among others, there may preferably be used urethane prepolymers obtained by reacting a polyester polyol with a polyisocyanate, the polyester polyol being prepared, for example, from a combination of adipic acid and propylene glycol and represented by the structural formula (5):

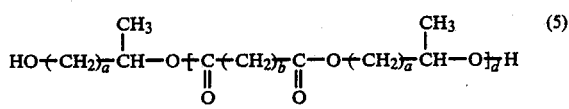

where a is a whole number of 1 to 5, b is a whole number of 4 to 10, and d is a whole number of 1 to 200.

Useful polyester polyols also include compounds formed by reacting a hydroxyl-containing higher fatty acid (such as ricinoleic acid) with glycerol, as well as castor oil and its derivatives. In this case, it is preferable to use tolylene diisocyanate, 4,4'-diphenylmethane diisocyanate or hexamethylene diisocyanate as the polyisocyanate. Among others, there may preferably be used urethane prepolymers of the structural formula (6):

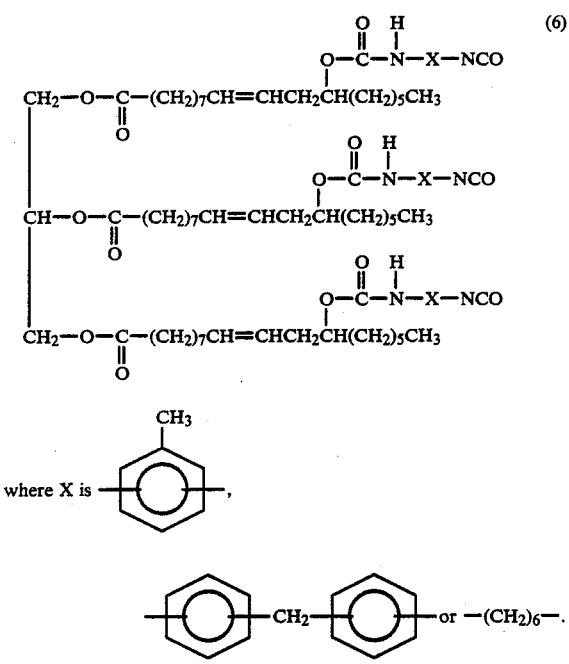

These urethane prepolymers containing one or more isocyanate groups serve to achieve bonding between a restorative material and a tooth by the reaction of the isocyanate group(s) present in the molecule, with the principal organic components constituting living tooth tissues and, in particular, dentin (especially collagen containing a large number of active hydrogen radicals in the molecule), as well as water (body fluid). Among others, urethane prepolymers containing two or more free isocyanate groups per molecule are preferred because they can exhibit excellent bonding properties.

The above-described urethane prepolymers containing one or more isocyanate groups can be used alone. However, in order to improve the workability of the composition, they may be used in combination with a diluent inert to the isocyanate group, such as acetone, methyl ethyl ketone, ethyl acetate, toluene, xylene or trichloroethane.

Basically, a dental adhesive composition comprising component (a) alone would exhibit the desired adhesivity. However, where it is intended to carry out bonding operation in the oral cavity, restrictions are often imposed on the time required to cure the adhesive layer. Thus, the radical-polymerizable unsaturated monomer used as component (b) in the compositions of the present invention is a component required to rapidly harden the adhesive layer by exposure to light in the presence of the photopolymerization initiator used as component (c). For this purpose, there may be used any radical-polymerizable unsaturated monomer that does not interfere with the adhesivity of component (a). Useful unsaturated monomers include monofunctional and multifunctional unsaturated monomers.

Specific examples of useful monofunctional unsaturated monomers include methyl (meth)acrylate, ethyl (meth)acrylate, propyl (meth)acrylate, butyl (meth)acrylate, pentyl (meth)acrylate, hexyl (meth)acrylate, 2-hydroxyethyl (meth)acrylate, glycidyl (meth)acrylate, benzyl (meth)acrylate, vinyl acetate, styrene and acrylonitrile. Especially preferred are methyl acrylate, methyl methacrylate, 2-hydroxyethyl methacrylate, vinyl acetate and benzyl methacrylate.

Useful bifunctional unsaturated monomers include, for example, polyethylene glycol di(meth)-acrylates of the general formula (7):

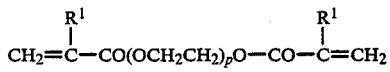

where $R^1$ is a hydrogen atom or a methyl group, and p is a whole number of 1 to 20. Specific examples thereof include ethylene glycol di(meth)acrylate, diethylene glycol di(meth)acrylate, triethylene glycol di(meth)acrylate, tetraethylene glycol di(meth)acrylate, pentaethylene glycol di(meth)acrylate, hexaethylene glycol di(meth)acrylate, heptaethylene glycol di(meth)-acrylate, octaethylene glycol di(meth)acrylate, nonacethylene glycol di(meth)acrylate, decaethylene glycol di(meth)acrylate, polyethylene glycol di(meth)-acrylates of the general formula (7) in which P is 14, polyethylene glycol di(meth)acrylates of the general formula (7) in which p is 17, and polyethylene glycol di(meth)acrylates of the general formula (7) in which p is 19. Especially preferred are ethylene glycol di(meth)acrylate, triethylene glycol di(meth)acrylate, nonaethylene glycol di(meth)acrylate, and polyethylene glycol di(meth-)acrylates of the general formula (7) in which p is 14. Moreover, there may also be used urethane di(meth)acrylates of the general formula (8):

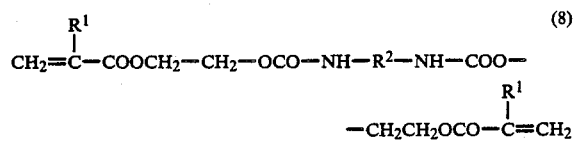

where $R^1$ is a hydrogen atom or a methyl group, and $R^2$ is an alkylene group of 1 to 8 carbon atoms, or

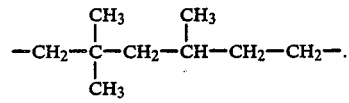

Specific examples thereof include di(acryloxyethyl)-dimethylene diurethane, di-(methacryloxyethyl)-dimethylene diurethane, di(acryloxyethyl)tetramethylene diurethane, di(methacryloxyethyl)-tetramethylene diurethane, di(acryloxyethyl)-trimethylhexamethylene diurethane, and di(methcryloxyethyl)-trimethylhexanmethylene diurethane. Especially preferred is the urethane dimethacrylate of the structural formula (9):

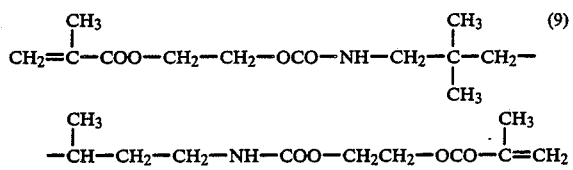

Furthermore, there may also be used 1,6-hexanediol di(meth)acrylate, neopentyl glycol di(meth)acrylate and trimethylolpropane tri(meth)-acrylate. Especially preferred is trimethylolpropane triacrylate.

Furthermore, there may also be used (meth)-acrylate compounds having a bisphenol A skeleton and represented by the general formula (10) or (11):

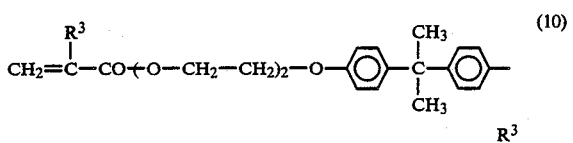

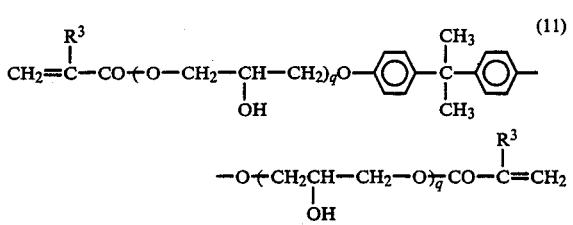

where $R^3$ is a hydrogen atom or a methyl group, and q is a whole number of 1 to 20.

Specific examples thereof include 2,2-bis(4-methacryloxypolyethoxyphenyl)propanes, 2,2-bis [4-(3-methacryloxy-2-hydroxypropoxy)phenyl]propane, 1,2-bis[3-(meth)acryloyloxy-2-hydroxypropoxy]ethane and 1,4-bis[3-(meth)acryloyloxy-2-hydroxypropoxy]butane.

Useful tetrafunctional unsaturated monomers include, for example, tetrafunctional urethane (meth)-acrylates having the general formula (12):

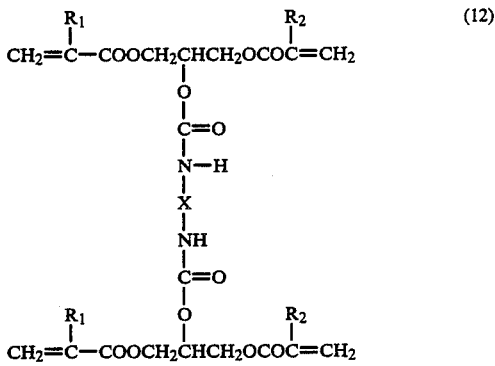

(12)

where $R_1$ and $R_2$ are hydrogen atoms or methyl groups, and X is $-CH_2-$, $-CH_2CH_2-$, $-(CH_2)_3-$, $-(CH_2)_4-$, $-(CH_2)_5-$, $-(CH_2)_6-$ or

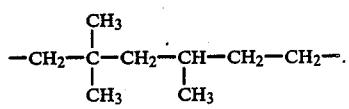

Specific and preferred examples thereof include the tetrafunctional urethane (meth)acrylate of the general formula (12) in which $R_1$ is a hydrogen atom, $R_2$ is a methyl group, and X is $-(CH_2)_6-$ (hereinafter referred to as U-4HA) and the tetrafunctional methacrylate of the general formula (12) in which $R_1$ and $R_2$ are methyl groups and X is $-(CH_2)_6-$ (hereinafter referred to as U-4H).

In addition, there may preferably be used hexafunctional urethane (meth)acrylates having an isocyanuric acid skeleton and represented by the general formula (13):

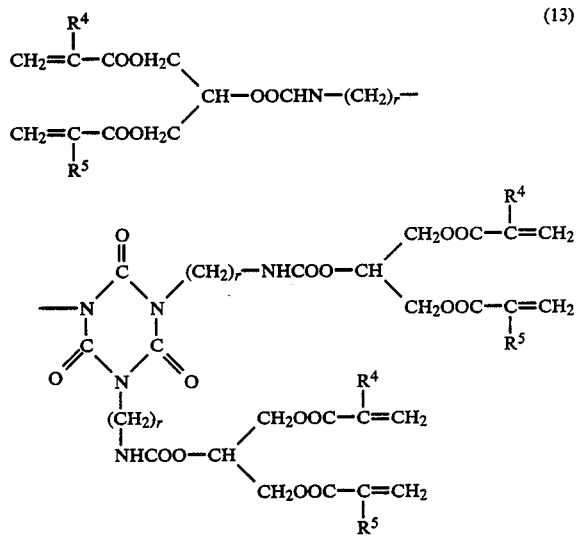

(13)

where $R_4$ and $R_5$ are hydrogen atoms or methyl groups, and r is a whole number of 1 to 10. Specific examples thereof include the compound of the general formula (13) in which r is 6, $R^4$ is a hydrogen atom, and $R^5$ is a methyl group (hereinafter referred to as U-6HA) and the compound of the general formula (13) in which r is 6 and both $R^4$ and $R^5$ are hydrogen atoms (hereinafter referred to as U-6H). These compounds are especially preferred hexafunctional unsaturated monomers.

The foregoing radical-polymerizable unsaturated monomers may be used either alone or in admixture.

The photopolymerization initiator used as component (c) in the composition of the present invention may be selected from conventionally known ultraviolet light polymerization initiators (such as benzophenone) and visible light polymerization initiators, according to the intended purpose of use. Where the composition of the present invention is to be used in the oral cavity, it is preferable to use a photopolymerization initiator capable of initiating the polymerization in response to visible light in the wavelength range of about 400 to 1,200 nm and free of near-ultraviolet radiation which might be harmful to the oral mucosa. Accordingly, it is preferable that the photosensitizer included in the photopolymerization initiator be one which can be excited by visible light in the wavelength range of about 400 to 1,200 nm. The compounds which can be used for this purpose are, for example, α-diketone compounds. Specific examples of useful α-diketone compounds include camphorquinone, benzil and diacetyl. Among others, camphorquinone is especially preferred because of its high polymerization activity.

In order to achieve desired excellent photopolymerizability, it is desirable to use a visible light polymerization initiator comprising a combination of a photosensitizer as described above and a reducing agent such as a tertiary amine. Specific examples of useful tertiary amines include aliphatic amines such as trimethylamine, triethylamine and tripropylamine; and aromatic amines such as isoamyl 4-(N,N-dimethylamino)-benzoate, hexyl 4-(N,N-dimethylamino)benzoate, heptyl 4-(N,N-dimethylamino)benzoate, octyl 4-(N,N-dimethylamino)benzoate, 4,4'-bis(dimethylamino)benzophenone, 4,4'-bis(diethylamino)benzophenone and 4,4'-bis(dibutylamino)benzophenone. Among others, aromatic tertiary amines are preferred. In particular, isoamyl 4-(N,N-dimethylamino)benzoate, 4,4'-bis(dimethylamino)-benzophenone and 4,4'-bis(diethylamino)-benzophenone are most preferred because excellent visible light polymerizing activity can be obtained by using them in combination with camphorquinone.

The amounts in which these visible light polymerization initiators may be added have their respective appropriate ranges, depending on the types of photosensitizer and reducing agent used. For example, in the camphorquinone/isoamyl 4-(N,N-dimethylamino)benzoate system, camphorquinone is preferably added in an amount of 0.01 to 25% by weight, more preferably 0.05 to 15% by weight, based on the radical-polymerizable unsaturated monomer, and isoamyl 4-(N,N-dimethylamino)benzoate is preferably added in an amount of 0.05 to 30% by weight, more preferably 0.1 to 25% by weight. Similarly, in the camphorquinone/4,4-bis(-dimethylamino)benzophenone system, camphorquinone is preferably added in an amount of 0.005 to 30% by weight, more preferably 0.03 to 20% by weight, based on the radical-polymerizable unsaturated monomer, and 4,4'-bis(dimethylamino)-benzophenone is preferably added in an amount of 0.01 to 25% by weight, more preferably 0.05 to 20% by weight.

In the dental adhesive compositions of the present invention, the weight ratio of component (a) to component (b) can range from 1:150 to 150:1 and more preferably from 1:100 to 100:1. In order to obtain adhesivity sufficient for practical purposes, the weight ratio most preferably ranges from 1:50 to 50:1.

Although the dental adhesive compositions of the present invention consisting essentially of the above-defined components (a), (b) and (c) exhibit adhesivity sufficient for practical purposes, further research has demonstrated that greater adhesivity can be obtained by adding thereto a polymerizable phosphoric ester compound of the general formula (1):

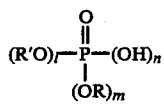

where R is a group selected from the class consisting of

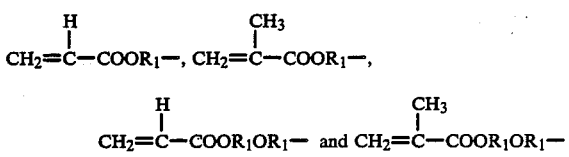

in which $R_1$ is an alkylene group having carbon atoms 2-12, R' is an alkyl or 2, m is 1 or 2, l is 0 or 1, and the sum of (n+m+l) is equal to 3.

Specific examples of the polymerizable phosphoric ester compound include

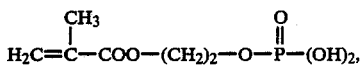
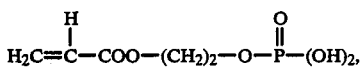
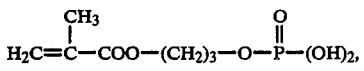
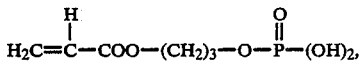
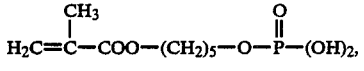
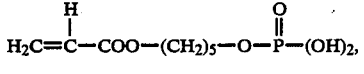
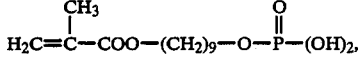
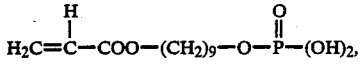
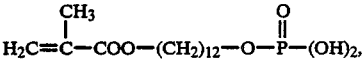
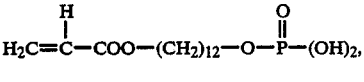
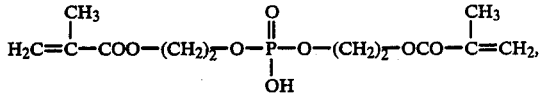

-continued

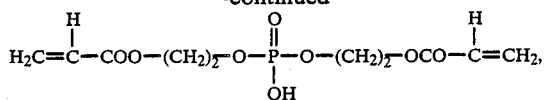
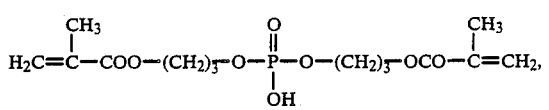
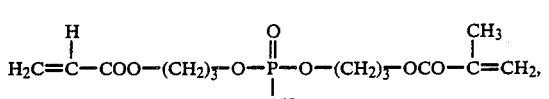
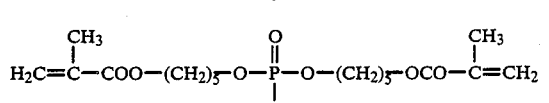

and

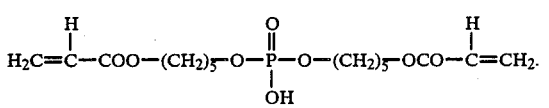

Among these polymerizable phosphoric ester compounds, methacryloxyethyl phosphate of the formula

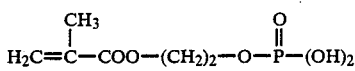

and dimethacryloxyethyl phosphate of the formula

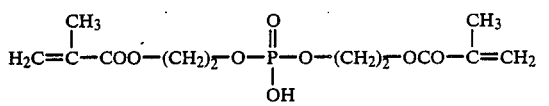

are especially preferred.

The polymerizable phosphoric ester compound is usually used in an amount of 0.1 to 30 parts by weight, preferably 0.5 to 10 parts by weight, and more preferably 1.0 to 5.0 parts by weight, per 100 parts by weight of the radical-polymerizable unsaturated monomer used as component (b).

The dental adhesive compositions of the present invention consist essentially of the above-defined three or four components. If necessary, however, they may additionally contain inorganic fillers (such as silica powder, quartz powder and various glass powders), organic polymers (such as polymethyl methacrylate and polystyrene), colorants, polymerization inhibitors (such as hydroquinone and methylphenol), antioxidants, ultraviolet light absorbers, pigments and dyes.

In ordinary cases, the dental adhesive compositions of the present invention may conveniently be stored, till use, in the form of mixtures consisting of the aforesaid three or four components. Alternatively, it is also possible to separately store components (a) and a mixture of components (b), (c) and optionally (d), and mix them immediately before use.

As the light source (in particular, visible light source) for curing the dental adhesive compositions of the present invention in a short time, there may be used light emitted by a halogen lamp, xenon lamp, mercury vapor lamp or fluorescent lamp and having wavelengths in the range of 3,500 to 12,000 ° Å.

The dental adhesive compositions of the present invention can be applied to a variety of restorative materials. More specifically, they have excellent bonding properties not only to heat-curable materials commonly used as prosthetic materials in the art, including composite resins (i.e., composite materials obtained by blending a multifunctional monomer with an inorganic filler) and crown resins, but also to thermoplastic resins for use in denture bases (such as polymethyl methacrylate, polysulfone and polycarbonate), various cementing materials, amalgam, alumina, gold and alloys.

When used to bond a restorative material to living tooth tissues, especially to dentin, the dental adhesive compositions of the present invention can exhibit adhesivity sufficient for practical purposes, without requiring any troublesome pretreatment with an etching agent (such as phosphoric acid) that has been indispensable in the prior art. Moreover, owing to their photopolymerizability, the dental adhesive compositions of the present invention can be hardened in a short time by exposure to light before their inherent adhesivity is exhibited. Thus, they are easy to handle in the oral cavity.

The present invention is further illustrated by the following examples. However, these examples are not to be construed to limit the scope of the invention.

[Preparation of restorative material A (visible light curable composite resin)]

| Ingredient | Amount |
|---|---|
| 2,2-Bis[4-(methacryloxyethoxy)phenyl]propane (hereinafter referred to as Bis-MEPP) | 8 g |
| Triethylene glycol dimethacrylate (hereinafter referred to as 3G) | 12 g |
| Silanated quartz powder (with an average particle diameter of about 4 μm) | 74 g |
| Finely powdered silicon dioxide (#R-972; trade name; a product of Nippon Aerosil Co.) | 6 g |
| Camphorquinone | 0.4 g |
| Isoamyl 4-(N,N-dimethylamino)benzoate | 2 g |

According to the above formulation, a visible light curable composite resin (i.e., a pasty mixture consisting of multifunctional monomers, inorganic fillers and a visible light polymerization initiator) was prepared in a dark room to obtain restorative material A.

[Preparation of restorative material B (visible light curable crown resin)]

| Ingredient | Amount |
|---|---|
| 2,2-Bis[4-(3-methacryloxy-2-hydroxypropoxy)phenyl]propane (hereinafter referred to as Bis-GMA) | 40 g |
| 3G | 60 g |
| Camphorquinone | 0.7 g |
| Isoamyl 4-(N,N-dimethylamino)benzoate | 2.8 g |

According to the above formulation, a visible light curable crown resin (i.e., a mixture consisting of multifunctional monomers and a visible light polymerization initiator) was prepared in a dark room to obtain restorative material B.

[Procedure for the evaluation of bonding properties and method for the measurement of bond strength]

(1) A freshly extracted cattle fore-tooth was cut with a precision cutter (Isomet; trade name; a product of Bühler Co.) to expose a flat dentin surface and a flat enamel surface. Then, using a piece of No. 1000 water-resistant abrasive paper, these exposed surfaces were fully polished under a stream of water. In some cases, the enamel surface was etched with a phosphoric acid etchant (manufactured by GC Dental Industries Co.) in the usual manner.

(2) A dental adhesive composition was applied to the dentin surface or the enamel surface. Any volatile components such as a solvent were scattered and evaporated by exposure to a stream of air for about 10 seconds.

(3) A cylindrical silicone ring (openable on one side) having an inner diameter of about 5 mm, a height of about 5 mm and a wall thickness of about 3 mm was placed on the surface to which the dental adhesive composition had been applied. Then, the silicone ring was filled with a liquid restorative material to a height of about 3 mm.

(4) The aperture of a visible light projector (GC Light; trade name; manufactured by GC Dental Industries Co.) was brought into contact with the upper end of the silicone ring filled with the restorative material Thus, the restorative material and the adhesive composition were cured by exposure to visible light for 60 seconds.

(5) After the lapse of about 10 minutes, the silicone ring was removed to obtain a specimen having the restorative material bonded to the surface of the tooth sample.

(6) After the entire specimen was stored in water at 37° C. for a predetermined period of time, a spacer for bonding test (i.e., an acrylic rod having the same diameter as the restorative material) was joined to the top of the restorative material by means of GC Unifast Quick Self-Curing Acrylic Resine (Uni Fast; trade name; manufactured by GC Dental Industries Co.). The resulting assembly was mounted on a testing jig and subjected to a tensile test for the measurement of bond strength. The measuring conditions were as follows.

Tensile tester: Tensilon (trade name; manufactured by Toyo-Baldwin Co.).
Crosshead speed (pulling speed): 0.5 mm/min.
Chart speed: 10 mm/min.
Full scale: 5 kgW or 20 kgW.
Number of specimens: n=3.

[Synthesis of isocyanate-containing urethane prepolymers (I)]

Using propylene glycol as an active hydrogen compound, ring opening copolymerization of propylene oxide and ethylene oxide was carried out according to conventional procedure. Thus, there were obtained various polyether glycols containing ethylene oxide units (hereinafter referred to as EO) and propylene oxide units (hereinafter referred to as PO) in varying molar ratios and having different molecular weights, as shown in Table 1.

Then, according to conventional procedure, these polyether glycols were reacted with an isocyanating agent comprising tolylene diisocyanate (containing 2,4- and 2,6-isomers in a molar ratio of 80:20; hereinafter referred to as TDI), 4,4-diphenylmethane diisocyanate (hereinafter referred to as MDI) or hexamethylene diisocyanate (hereinafter referred to as HDI). In this reaction, the polyether glycol and the isocyanating agent were used in a molar ratio of 1:2. Thus, there were obtained various urethane prepolymers containing two terminal isocyanate groups and having the codes shown in Table 1.

used in a molar ratio of 1:1. Thus, there were obtained various urethane prepolymers containing one terminal

TABLE 1

| Code for prepolymer containing two terminal isocyanate groups | Composition of polyether glycol | | | | Isocyanating agent | Property of prepolymer |
|---|---|---|---|---|---|---|
| | EO/PO | Type of polymer | Average molecular weight | Code | | |
| TPT-1 | 0/100 | — | 500 | PEP-1 | TDI | Hydrophobic |
| TPT-2 | " | — | 3,000 | PEP-2 | " | " |
| TPT-3 | " | — | 18,000 | PEP-3 | " | " |
| TPT-4 | 20/80 | Random | 8,000 | PEP-4 | " | " |
| TPT-5 | " | " | 7,000 | PEP-5 | " | " |
| TPT-6 | " | Block | 1,500 | PEP-6 | " | " |
| TPT-7 | 40/60 | Random | 1,000 | PEP-7 | " | Hydrophilic |
| TPT-8 | " | " | 5,000 | PEP-8 | " | " |
| TPT-9 | " | Block | 3,000 | PEP-9 | " | " |
| TPT-10 | 60/40 | Random | 400 | PEP-10 | " | Water-soluble |
| TPT-11 | " | " | 2,000 | PEP-11 | " | " |
| TPT-12 | " | " | 10,000 | PEP-12 | " | " |
| TPT-13 | 80/20 | Random | 600 | PEP-13 | " | " |
| TPT-14 | " | " | 1,200 | PEP-14 | " | " |
| MPM-1 | 0/100 | — | 500 | PEP-1 | MDI | Hydrophobic |
| MPM-2 | 20/80 | Random | 7,000 | PEP-5 | " | " |
| MPM-3 | 40/60 | Random | 1,000 | PEP-7 | " | Hydrophilic |
| MPM-4 | " | " | 5,000 | PEP-8 | " | " |
| MPM-5 | " | Block | 3,000 | PEP-9 | " | " |
| MPM-6 | 60/40 | Random | 2,000 | PEP-11 | " | Water-soluble |
| HPH-1 | 0/100 | — | 500 | PEP-1 | HDI | Hydrophobic |
| HPH-2 | 20/80 | Random | 7,000 | PEP-5 | " | " |
| HPH-3 | 40/60 | Random | 1,000 | PEP-7 | " | Hydrophilic |
| HPH-4 | " | " | 5,000 | PEP-8 | " | " |
| HPH-5 | " | Block | 3,000 | PEP-9 | " | " |
| HPH-6 | 60/40 | Random | 2,000 | PEP-11 | " | Water-soluble |

[Synthesis of isocyanate-containing urethane prepolymers (II)]

In the same manner as described in the foregoing synthesis of urethane prepolymers (I), various polyether glycols were reacted with an isocyanating agent comprising TDI, MDI or HDI. In this case, however, the polyether glycol and the isocyanating agent were used in a molar ratio of 1:1. Thus, there were obtained various urethane prepolymers containing one terminal isocyanate group and one terminal hydroxyl group and having the codes shown in Table 2.

TABLE 2

| Code for prepolymer contg. one terminal isocyanate group | Composition of polyether glycol | | | | Isocyanating agent |
|---|---|---|---|---|---|
| | EO/PO | Type of polymer | Average molecular weight | Code | |
| PT-1 | 0/100 | — | 500 | PEP-1 | TDI |
| PT-2 | 20/80 | Random | 7,000 | PEP-5 | " |
| PT-3 | 40/60 | Random | 1,000 | PEP-7 | " |
| PT-4 | " | " | 5,000 | PEP-8 | " |
| PT-5 | " | Block | 3,000 | PEP-9 | " |
| PT-6 | 60/40 | Random | 2,000 | PEP-11 | " |
| PM-1 | 40/60 | Random | 1,000 | PEP-7 | MDI |
| PM-2 | " | " | 5,000 | PEP-8 | " |
| PM-3 | " | Block | 3,000 | PEP-9 | " |
| PH-1 | 40/60 | Random | 1,000 | PEP-7 | HDI |
| PH-2 | " | " | 5,000 | PEP-8 | " |
| PH-3 | " | Block | 3,000 | PEP-9 | " |

[Synthesis of isocyanate-containing urethane prepolymers (III)]

Some of the urethane prepolymers containing two terminal isocyanate groups, which had been obtained in the foregoing synthesis of urethane prepolymers (I), were reacted with a hydroxyl-containing radical-polymerizable unsaturated monomer comprising 2-hydroxyethyl methacrylate. In this reaction, the urethane prepolymer and the unsaturated monomer were used in a molar ratio of 1:1. Thus, there were obtained various urethane prepolymers containing one terminal radical-polymerizable vinyl group and one terminal isocyanate group and having the codes shown in Table 3.

TABLE 3

| Code for urethane prepolymer contg. one terminal radical-polymerizable vinyl group and one terminal isocyanate group | Starting urethane prepolymer contg. two terminal isocyanate groups | Unsaturated monomer used to introduce a terminal radical-polymerizable vinyl group |
|---|---|---|
| TV-1 | TPT-7 | 2-Hydroxyethyl methacrylate |
| TV-2 | TPT-10 | 2-Hydroxyethyl methacrylate |
| TV-3 | TPT-13 | 2-Hydroxyethyl methacrylate |
| MV-1 | MPM-3 | 2-Hydroxyethyl methacrylate |
| HV-1 | HPH-3 | 2-Hydroxyethyl methacrylate |

[Synthesis of vinyl-containing urethane prepolymers (IV)]

Some of the urethane prepolymers containing two terminal isocyanate groups, which had been obtained in the foregoing synthesis of urethane prepolymers (I), were reacted with a hydroxyl-containing radical-polymerizable unsaturated monomer comprising 2-hydroxyethyl methacrylate. In this reaction, the urethane prepolymer and the unsaturated monomer were used in a molar ratio of 1:2. Thus, there were obtained various urethane prepolymers containing two terminal radical-polymerizable vinyl groups and having the codes shown in Table 4.

TABLE 4

| Code for urethane prepolymer contg. two terminal radical-polymerizable vinyl groups | Starting urethane prepolymer contg. two terminal isocyanate groups | Unsaturated monomer used to introduce a terminal radical-polymerizable vinyl group |
|---|---|---|
| DV-1 | TPT-7 | 2-Hydroxyethyl methacrylate |
| DV-2 | MPM-3 | 2-Hydroxyethyl methacrylate |
| DV-3 | HPH-3 | 2-Hydroxyethyl methacrylate |

[Synthesis of isocyanate-containing urethane prepolymers (V)]

Adipic acid and propylene glycol were mixed in a molar ratio ranging from 1:1.1 to 1:1.5. Then, using magnesium acetate as the catalyst, polycondensation of these compounds was carried out according to conventional procedure. Thus, there were obtained various polyester glycols containing hydroxyl groups at both ends and having different molecular weights. The codes for these polyester glycols are shown in Table 5.

Then, according to conventional procedure, these polyester glycols were reacted with an isocyanating agent comprising TDI, MDI or HDI. In this reaction, the polyester glycol and the isocyanating agent were used in a molar ratio of 1:2. Thus, there were obtained various urethane prepolymers containing two terminal isocyanate groups and having the codes shown in Table 5.

TABLE 5

| Code for urethane prepolymer contg. two terminal isocyanate groups | Polyester glycol | | Isocyanating agent |
|---|---|---|---|
| | Code | Average molecular weight | |
| TS-1 | SG-2 | 1,000 | TDI |
| TS-2 | SG-4 | 5,000 | " |
| MS-1 | SG-1 | 500 | MDI |
| MS-2 | SG-2 | 1,000 | " |
| MS-3 | SG-3 | 2,000 | " |
| MS-4 | SG-4 | 5,000 | " |
| MS-5 | SG-5 | 10,000 | " |
| MS-6 | SG-6 | 18,000 | " |
| HS-1 | SG-2 | 1,000 | HDI |
| HS-2 | SG-4 | 1,000 | " |

[Synthesis of isocyanate-containing urethane prepolymers (VI)]

In the same manner as described in the foregoing synthesis of urethane prepolymers (V), various polyester glycols were reacted with an isocyanating agent comprising TDI, MDI or HDI. In this case, however, the polyester glycol and the isocyanating agent were used in a molar ratio of 1:1. Thus, there were obtained various urethane prepolymers containing one terminal isocyanate group and one terminal hydroxyl group and having the codes shown in Table 6.

TABLE 6

| Code for urethane prepolymer contg. one terminal isocyanate group | Polyester glycol | | Isocyanating agent |
|---|---|---|---|
| | Code | Average molecular weight | |
| TH-1 | SG-2 | 1,000 | TDI |
| TH-2 | SG-4 | 5,000 | " |
| MH-1 | SG-2 | 1,000 | MDI |
| MH-2 | SG-3 | 2,000 | " |
| MH-3 | SG-4 | 5,000 | " |
| MH-4 | SG-5 | 10,000 | " |
| HH-1 | SG-2 | 1,000 | HDI |
| HH-2 | SG-4 | 1,000 | " |

[Synthesis of isocyanate-containing urethane prepolymers (VII)]

According to conventional procedure, castor oil used as a polyol compound was reacted with an isocyanating agent comprising TDI, MDI or HDI. In this reaction, the polyol compound and the isocyanating agent were used in a molar ratio of 1:3. Thus, there were obtained three urethane prepolymers containing three free isocyanate groups. The molar ratio was calculated on the assumption that castor oil had the structure of ricinoleic acid triglyceride and contained no impurities.

The resulting urethane prepolymers containing three free isocyanate groups were given their respective codes according to the type of the isocyanating agent used. Specifically, the codes were CO-1 for TDI, CO-2 for MDI, and CO-3 for HDI.

[Synthesis of isocyanate-containing urethane prepolymers (VIII)]

The urethane prepolymers containing three free isocyanate groups, which had been obtained in the foregoing synthesis of urethane prepolymers (VII), were reacted with a hydroxyl-containing radical-polymerizable unsaturated monomer comprising 2-hydroxyethyl methacrylate. In this reaction, the urethane prepolymer and the unsaturated monomer were used in a molar ratio of 1:1 or 1:2. Thus, there were obtained three urethane prepolymers containing one radical-polymerizable vinyl group and two free isocyanate groups and having the codes shown in Table 7, as well as three urethane prepolymers containing two radical-polymerizable vinyl groups and one free isocyanate group and having the codes shown in Table 7.

TABLE 7

| Code for the resulting urethane prepolymer contg. one (two) radical-polymerizable vinyl group and two (one) free isocyanate groups | Starting urethane prepolymer contg. three free isocyanate groups | Hydroxy-contg. radical-polymerizable vinyl monomer used | Molar ratio |
|---|---|---|---|
| SV-1 | CO-1 | 2-Hydroxyethyl methacrylate | 1/1 |
| SV-2 | CO-2 | 2-Hydroxyethyl methacrylate | " |
| SV-3 | CO-3 | 2-Hydroxyethyl methacrylate | " |
| VV-1 | CO-1 | 2-Hydroxyethyl methacrylate | 1/2 |
| VV-2 | CO-2 | 2-Hydroxyethyl | " |

TABLE 7-continued

| Code for the resulting urethane prepolymer contg. one (two) radical-polymerizable vinyl group and two (one) free isocyanate groups | Starting urethane prepolymer contg. three free isocyanate groups | Hydroxy- contg. radical- polymerizable vinyl monomer used | Molar ratio |
|---|---|---|---|
| VV-3 | CO-3 | 2-Hydroxyethyl methacrylate methacrylate | " |

[Synthesis of vinyl-containing urethane prepolymers (IX)]

The urethane prepolymers containing three free isocyanate groups, which had been obtained in the foregoing synthesis of urethane prepolymers (VII), were reacted with a hydroxyl-containing radical-polymerizable unsaturated monomer comprising 2-hydroxyethyl methacrylate. In this case, the urethane prepolymer and the unsaturated monomer were used in a molar ratio of 1:3. Thus, there were obtained three urethane prepolymers containing three radical-polymerizable vinyl groups.

The resulting urethane prepolymers containing three radical-polymerizable vinyl groups were given their respective codes according to the type of the starting urethane prepolymer containing three free isocyanate groups. Specifically, the codes were PV-1 for CO-1, PV-2 for CO-2, and PV-3 for CO-3.

[Preparation of radical-polymerizable unsaturated monomer/visible light polymerization initiator mixtures]

Using a general-purpose mixer, various mixtures consisting of at least one radical-polymerizable unsaturated monomer and a visible light polymerization initiator were prepared in a dark room. The compositions of these mixtures and their respective codes are shown in Tables 8 to 10.

The code "EDMA" given in the tables as the designation of a radical-polymerizable unsaturated monomer refers to the urethane dimethacrylate of the structural formula

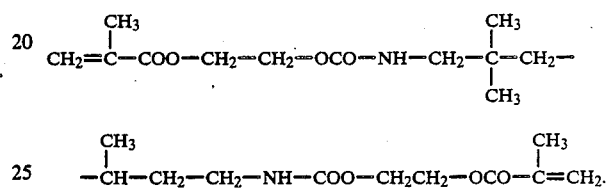

TABLE 8

| Code for radical-poly- merizable unsat. mono- mer/visible/ light poly- merization initiator mixture | Radical-polymerizable unsat. monomer and amount used (g) | | | | | | | | | Visible light polymerization initiator and amount used (g) | | |
|---|---|---|---|---|---|---|---|---|---|---|---|---|
| | Methyl- acry- late | Methyl metha- crylate | Butyl acry- late | Vi- nyl ace- tate | Ethylene glycol dimeth- acrylate | Tri- ethylene glycol dimeth- acrylate | Nona- ethylene glycol diacry- late | EDMA | Trimeth- ylol- propane trimeth- acrylate | Cam- phor- qui- none | Isoamyl 4- (N,N-di methyl- amino)- benzoate | 4,4'-Bis- (dimeth- ylamino)- benzo- phenone |
| LC-1 | — | — | — | — | 100 | — | — | — | — | 0.8 | 1.2 | — |
| LC-2 | — | — | — | — | 100 | — | — | — | — | " | — | 1.2 |
| LC-3 | — | — | — | — | — | 100 | — | — | — | " | 1.2 | — |
| LC-4 | — | — | — | — | — | 100 | — | — | — | " | — | 1.2 |
| LC-5 | — | — | — | — | — | — | — | 100 | — | " | 1.2 | — |
| LC-6 | — | — | — | — | — | — | — | 100 | — | " | — | 1.2 |
| LC-7 | — | 55 | — | — | — | — | 45 | — | — | 1.2 | 1.6 | — |
| LC-8 | — | 55 | — | — | — | — | 45 | — | — | " | — | 1.6 |
| LC-9 | 55 | — | — | — | — | 45 | — | — | — | " | 1.6 | — |
| LC-10 | 55 | — | — | — | — | 45 | — | — | — | " | — | 1.6 |
| LC-11 | — | — | 35 | — | — | 65 | — | — | — | " | 1.6 | — |
| LC-12 | — | — | 35 | — | — | 65 | — | — | — | " | — | 1.6 |
| LC-13 | — | — | — | 25 | — | — | 75 | — | — | " | 1.6 | — |
| LC-14 | — | — | — | 25 | — | — | 75 | — | — | " | — | 1.6 |
| LC-15 | — | 70 | — | — | — | — | 30 | — | — | 1.5 | 2.0 | — |
| LC-16 | — | 70 | — | — | — | — | 30 | — | — | " | — | 2.0 |
| LC-17 | — | 85 | — | — | — | — | 15 | — | — | " | 2.0 | — |
| LC-18 | — | 85 | — | — | — | — | 15 | — | — | " | — | 2.0 |
| LC-19 | — | 30 | — | — | — | — | — | 70 | — | 0.5 | 1.0 | — |

TABLE 9

| Code for radical- polymerizable unsat. monomer/ visible light poly. initiator mixture | Radical-polymerizable unsat. monomer and amount used (g) | | | | | | | Visible light poly. initiator and amount used (g) | | |
|---|---|---|---|---|---|---|---|---|---|---|
| | Methyl acryl- late | 2-Hydroxy- ethyl meth- acrylate | Neopentyl glycol dimeth- acrylate | Trimethylene glycol dimeth- acrylate | Bis-GMA | U-4HA | U-6HA | Com- phor- qui- none | Isoamyl 4- (N,N- dimethyl- amino)- benzoate | 4,4'-Bis- (dimeth- ylamino)- benzo- phenone |
| LC-20 | — | — | 100 | 40 | 60 | — | — | 0.8 | 1.2 | — |
| LC-21 | — | — | 100 | 40 | 60 | — | — | " | — | 1.2 |
| LC-22 | — | 40 | — | — | — | 60 | — | " | 1.2 | — |
| LC-23 | — | 40 | — | — | — | 60 | — | " | — | 1.2 |
| LC-24 | — | — | 40 | — | — | — | 60 | " | 1.2 | — |
| LC-25 | — | — | 40 | — | — | — | 60 | " | — | 1.2 |
| LC-26 | — | 20 | 30 | — | 50 | — | — | " | 1.2 | — |
| LC-27 | — | 20 | 30 | — | 50 | — | — | " | — | 1.2 |

TABLE 9-continued

| Code for radical-polymerizable unsat. monomer/ visible light poly. initiator mixture | Radical-polymerizable unsat. monomer and amount used (g) | | | | | | | Visible light poly. initiator and amount used (g) | | |
|---|---|---|---|---|---|---|---|---|---|---|
| | Methyl acrylate | 2-Hydroxy-ethyl meth-acrylate | Neopentyl glycol dimeth-acrylate | Trimethylene glycol dimeth-acrylate | Bis-GMA | U-4HA | U-6HA | Comphor-qui-none | Isoamyl 4-(N,N-dimethyl-amino)-benzoate | 4,4'-Bis-(dimeth-ylamino)-benzo-phenone |
| LC-28 | — | 20 | — | 30 | — | 50 | — | 1.2 | 1.6 | — |
| LC-29 | — | 20 | — | 30 | — | 50 | — | " | — | 1.6 |
| LC-30 | 20 | — | 30 | — | — | — | 50 | " | 1.6 | — |
| LC-31 | 20 | — | 30 | — | — | — | 50 | 1.2 | — | 1.6 |
| LC-32 | — | — | 20 | 30 | — | — | 50 | " | 1.6 | — |
| LC-33 | — | — | 20 | 30 | — | — | 50 | " | — | 1.6 |
| LC-34 | — | 10 | 20 | 30 | 40 | — | — | " | 1.6 | — |
| LC-35 | — | 10 | 20 | 30 | 40 | — | — | " | — | 1.6 |

TABLE 10

| Code for radical-polymerizable unsat. monomer/ visible light poly. initiator mixture | Radical-polymericable unsat. monomer and amount used (g) | | | | | | | Visible light poly. initiator and amount used (g) | | |
|---|---|---|---|---|---|---|---|---|---|---|
| | Methyl acrylate | 2-Hydroxy ethyl acrylate | Neopentyl glycol dimeth-acrylate | Trimeth-ylene glycol dimeth-acrylate | Bis-GMA | U-4HA | U-6HA | Comphor-quinone | Isoamyl 4-(N,N-dimethyl-amino)benzoate | 4,4'-Bis-(dimeth-ylamino)-benzo-phenone |
| LC-36 | — | — | 40 | 60 | — | — | — | 0.8 | 1.2 | — |
| LC-37 | — | — | 40 | 60 | — | — | — | " | — | 1.2 |
| LC-38 | 20 | — | 20 | — | 60 | — | — | " | 1.2 | — |
| LC-39 | 20 | — | 20 | — | 60 | — | — | " | — | 1.2 |
| LC-40 | — | 20 | — | 20 | 20 | 40 | — | 1.2 | 1.6 | — |
| LC-41 | — | 20 | — | 20 | 20 | 40 | — | " | — | 1.6 |

[Preparation of radical-polymerizable unsaturated monomer/polymerizable phosphoric ester compound/visible light polymerization initiator mixtures]

Using a general-purpose mixer, various mixtures consisting of at least one radical-polymerizable unsaturated monomer (hereinafter referred to as monomer X), a polymerizable phosphoric ester compound (hereinafter referred to as monomer Z), and a visible light polymerization initiator were prepared in a dark room. The compositions of these mixtures and their respective codes are shown in Table 11.

TABLE 11

| Code for radical-polymerizable unsat. monomer/ visible light poly. initiator mixture | Radical-polymerizable unsat. monomer and amount used (g) | | | | | | | | | Visible light poly. initiator and amount used (g) | | |
|---|---|---|---|---|---|---|---|---|---|---|---|---|
| | Methyl acrylate | Methyl methacrylate | Butyl acrylate | Vinyl acetate | Ethylene glycol dimethacrylate | Triethylene glycol dimethacrylate | Nonaethylene glycol diacrylate | EDMA | Trimethylolpropane trimethacrylate | Camphorquinone | Isoamyl 4-(N,N-dimethylamino)benzoate | 4,4'-Bis(dimethylamino)benzophenone |
| LC-42 | — | — | — | — | 100 | — | — | — | — | 1.0 | 2.0 | — |
| LC-43 | — | — | — | — | 100 | — | — | — | — | " | " | 2.0 |
| LC-44 | — | — | — | — | — | — | 100 | — | — | " | 2.0 | — |
| LC-45 | — | — | — | — | — | — | 100 | — | — | " | " | — |
| LC-46 | — | — | — | — | — | — | — | — | 100 | " | 2.0 | — |
| LC-47 | — | — | — | — | — | — | — | — | 100 | " | " | 2.0 |
| LC-48 | — | 55 | — | — | — | — | — | 45 | — | 0.5 | 1.0 | — |
| LC-49 | — | 55 | — | — | — | — | — | 45 | — | " | " | 1.0 |
| LC-50 | 55 | — | — | — | — | 45 | — | — | — | " | 1.0 | — |
| LC-51 | 55 | — | — | — | — | 45 | — | — | — | " | " | 1.0 |
| LC-52 | — | — | 35 | — | — | — | 65 | — | — | 0.5 | 1.0 | 1.0 |
| LC-53 | — | — | 35 | — | — | — | 65 | — | — | " | " | 1.0 |
| LC-54 | — | — | — | 25 | — | — | — | 75 | — | " | 1.0 | — |
| LC-55 | — | — | — | 25 | — | — | — | 75 | — | " | " | 1.0 |
| LC-56 | — | 70 | — | — | — | — | — | 30 | — | 0.2 | 0.5 | — |
| LC-57 | — | 70 | — | — | — | — | — | 30 | — | " | " | 0.5 |
| LC-58 | — | 70 | — | — | — | — | — | 30 | — | " | 0.5 | — |
| LC-59 | — | 70 | — | — | — | — | — | — | 30 | " | " | 0.5 |
| LC-60 | — | — | — | 30 | — | — | — | — | 70 | 2.0 | 5.0 | — |

| Code for monomer X/ monomer Z/ visible light poly. initiator mixture | Monomer X, monomer Z and amounts used (g) | | | | | | | | | Visible light poly. initiator and amount (g) | | |
|---|---|---|---|---|---|---|---|---|---|---|---|---|
| | Acryloxy pivalate | Benzyl methacrylate | 2-Hydroxyethyl methacrylate | Triethylene glycol dimethacrylate | Bis-GMA | Bis-MEPP | U-4HA | U-6HA | Methacryloxyethyl phosphate | Dimethacryloxyethyl phosphate | Camphorquinone | Isoamyl 4-(N,N-dimethylamino)benzoate | 4,4'-Bis(dimethylamino)benzophenone |
| LC-61 | — | — | — | 40 | 60 | — | — | — | 2.0 | — | 0.8 | 1.2 | — |
| LC-62 | — | 20 | — | 40 | 60 | — | — | — | — | 2.0 | " | " | — |
| LC-63 | — | 20 | — | 20 | — | 60 | — | — | 2.0 | — | " | " | — |
| LC-64 | — | — | 40 | — | — | 60 | — | — | — | 2.0 | " | " | — |
| LC-65 | — | — | 40 | — | — | — | 60 | — | 2.0 | — | " | 1.2 | — |
| LC-66 | — | — | 20 | — | 20 | — | 60 | — | — | 2.0 | " | " | — |
| LC-67 | — | — | 20 | 20 | 20 | — | 40 | — | 2.0 | — | " | " | — |
| LC-68 | — | — | 30 | 30 | — | 30 | — | 40 | — | 2.0 | " | " | — |
| LC-69 | — | — | 30 | 10 | — | 30 | — | 30 | 2.0 | — | " | " | — |
| LC-70 | — | — | 30 | 10 | — | 30 | — | 30 | — | 2.0 | " | " | — |
| LC-71 | 100 | — | — | — | — | — | — | — | 2.0 | — | " | " | — |
| LC-72 | 100 | — | — | — | — | — | — | — | — | 2.0 | " | " | — |

| Code for monomer X/ monomer Z/ visible light poly. initiator mixture | Monomer X, monomer Z and amounts used | | | | | | | Visible light poly. initiator and amount (g) | | |
|---|---|---|---|---|---|---|---|---|---|---|---|
| | Acryloxy pivalate | 2-Hydroxyethyl methacrylate | Triethylene glycol dimethacrylate | 3G | Bis-MEPP | U-4HA | U-6HA | Methacryloxyethyl phosphate | Dimethacryloxyethyl phosphate | Camphorquinone | Isoamyl 4-(N,N-dimethylamino)benzoate | 4,4'-Bis(diethylamino)benzophenone |
| LC-73 | — | 30 | 10 | — | — | 30 | 30 | 0.2 | — | 0.8 | 1.2 | — |
| LC-74 | — | " | " | — | — | " | " | 0.2 | 0.2 | " | " | — |
| LC-75 | — | " | " | — | — | " | " | 0.6 | — | " | " | — |

TABLE 11-continued

| | | | | | | | | | | | | | |
|---|---|---|---|---|---|---|---|---|---|---|---|---|---|
| LC-76 | — | — | — | — | — | — | — | — | — | — | — | — | — |
| LC-77 | — | — | — | — | — | — | — | — | 4.0 | — | " | — | — |
| LC-78 | — | — | — | — | — | — | — | — | — | 0.6 | " | — | 1.2 |
| LC-79 | — | — | — | — | — | — | — | — | 7.0 | 4.0 | " | — | " |
| LC-80 | — | — | — | — | — | — | — | — | — | — | " | — | " |
| LC-81 | — | — | — | — | — | — | — | — | — | 7.0 | " | — | " |
| LC-82 | — | — | — | — | — | — | — | — | 20.0 | — | " | — | " |
| LC-83 | — | — | — | — | — | — | — | — | — | 20.0 | " | — | " |
| LC-84 | — | — | 30 | 40 | 60 | — | — | — | 2.0 | 2.0 | 0.8 | — | 1.2 |
| LC-85 | — | 20 | — | 10 | 30 | — | — | 30 | — | — | " | — | " |
| LC-86 | — | — | 40 | 20 | — | — | 60 | 60 | 2.0 | — | 1.2 | — | 1.6 |
| LC-87 | — | — | 30 | — | — | — | — | — | — | 2.0 | " | — | " |
| LC-88 | — | — | " | 10 | 30 | 10 | — | 30 | — | — | " | — | — |
| LC-89 | — | — | " | — | " | " | " | " | — | " | 0.8 | — | 1.2 |

EXAMPLES 1 TO 124

A series of adhesive compositions were prepared by mixing various urethane prepolymers containing two terminal isocyanate groups, which had been obtained in the foregoing synthesis of urethane prepolymers (I), with the radical-polymerizable unsaturated monomer/visible light polymerization initiator mixture LC-15 in a weight ratio of 1:1.

According to the above-described procedure for the evaluation of adhesivity and the above-described method for the measurement of bond strength, each of these adhesive compositions was used to bond restorative material A to an unetched dentin surface of a cattle tooth, and the resulting bond strength was measured. The results thus obtained are shown in Table 12.

Moreover, other series of adhesive compositions were prepared from various urethane prepolymers containing two terminal isocyanate groups and the radical-polymerizable unsaturated monomer/visible light polymerization initiator mixtures LC-15, LC-16, LC-22, LC-23, LC-56 and LC-57, and evaluated in the same manner. The results thus obtained are shown in Tables 12 to 16.

TABLE 12

| | Adhesive components | | Bond strength to dentin (kg/cm$^2$) After storage in water at 37° C. | |
|---|---|---|---|---|
| Example No. | Urethane prepolymer contg. two terminal isocyanate groups | Radical-polymerizable unsat. monomer/visible light poly. initiator mixture | for 1 day | for 7 days |
| 1 | TPT-1 | LC-15 | 23.0 | 23.3 |
| 2 | TPT-2 | " | 24.5 | 24.5 |
| 3 | TPT-3 | " | 23.8 | 24.0 |
| 4 | TPT-4 | " | 25.2 | 27.5 |
| 5 | TPT-5 | " | 24.8 | 27.0 |
| 6 | TPT-6 | " | 25.0 | 26.2 |
| 7 | TPT-7 | " | 28.7 | 30.0 |
| 8 | TPT-8 | " | 30.6 | 30.9 |
| 9 | TPT-9 | " | 27.0 | 29.3 |
| 10 | TPT-10 | " | 34.1 | 35.6 |
| 11 | TPT-11 | " | 33.5 | 36.0 |
| 12 | TPT-12 | " | 33.0 | 38.2 |
| 13 | TPT-13 | " | 36.3 | 40.0 |
| 14 | TPT-14 | " | 35.1 | 38.8 |
| 15 | MPM-1 | " | 18.7 | 19.7 |
| 16 | MPM-2 | " | 19.0 | 19.0 |
| 17 | MPM-3 | " | 23.0 | 25.1 |
| 18 | MPM-4 | " | 25.0 | 28.8 |
| 19 | MPM-5 | " | 30.2 | 30.5 |
| 20 | MPM-6 | " | 31.5 | 33.0 |
| 21 | HPH-1 | " | 20.0 | 20.0 |
| 22 | HPH-2 | " | 23.6 | 24.1 |
| 23 | HPH-3 | " | 28.1 | 29.0 |
| 24 | HPH-4 | " | 26.8 | 27.0 |
| 25 | HPH-5 | " | 27.0 | 28.6 |
| 26 | HPH-6 | " | 32.1 | 33.0 |

TABLE 13

| | Adhesive components | | Bond strength to dentin (kg/cm$^2$) After storage in water at 37° C. | |
|---|---|---|---|---|
| Example No. | Urethane prepolymer contg. two terminal isocyanate groups | Radical-polymerizabe unsat. monomer/visible light poly. initiator mixture | for 1 day | for 7 days |
| 27 | TPT-1 | LC-16 | 24.1 | 24.5 |
| 28 | TPT-2 | " | 23.3 | 24.0 |
| 29 | TPT-3 | " | 24.0 | 25.3 |
| 30 | TPT-4 | " | 26.6 | 28.1 |
| 31 | TPT-5 | " | 26.8 | 27.3 |
| 32 | TPT-6 | " | 28.0 | 29.0 |
| 33 | TPT-7 | " | 30.4 | 32.2 |
| 34 | TPT-8 | " | 31.5 | 33.0 |
| 35 | TPT-9 | " | 30.2 | 30.5 |
| 36 | TPT-10 | " | 37.0 | 39.0 |
| 37 | TPT-11 | " | 37.1 | 38.5 |
| 38 | TPT-12 | " | 36.9 | 38.0 |
| 39 | TPT-13 | " | 39.6 | 40.0 |
| 40 | TPT-14 | " | 37.0 | 37.0 |
| 41 | MPM-1 | " | 19.0 | 19.0 |
| 42 | MPM-2 | " | 17.2 | 17.5 |
| 43 | MPM-3 | " | 21.1 | 24.0 |
| 44 | MPM-4 | " | 27.0 | 28.5 |
| 45 | MPM-5 | " | 32.1 | 32.1 |
| 46 | MPM-6 | " | 33.7 | 34.0 |
| 47 | HPH-1 | " | 20.2 | 21.0 |
| 48 | HPH-2 | " | 22.4 | 23.5 |
| 49 | HPH-3 | " | 26.3 | 28.0 |
| 50 | HPH-4 | " | 27.5 | 28.0 |
| 51 | HPH-5 | " | 29.1 | 29.1 |
| 52 | HPH-6 | " | 30.3 | 31.5 |

TABLE 14

| | Adhesive components | | Bond strength to dentin (kg/cm$^2$) After storage in water at 37° C. | |
|---|---|---|---|---|
| Example No. | Urethane prepolymer contg. two terminal isocyanate groups | Radical-polymerizabe unsat. monomer/visible light poly. initiator mixture | for 1 day | for 7 days |
| 53 | TPT-1 | LC-22 | 25.1 | 25.5 |
| 54 | TPT-2 | " | 26.7 | 26.7 |
| 55 | TPT-3 | " | 26.0 | 26.2 |
| 56 | TPT-4 | " | 27.4 | 29.7 |

TABLE 14-continued

| Example No. | Adhesive components Urethane prepolymer contg. two terminal isocyanate groups | Radical-polymerizabe unsat. monomer/visible light poly. initiator mixture | Bond strength to dentin (kg/cm²) After storage in water at 37° C. for 1 day | for 7 days |
|---|---|---|---|---|
| 57 | TPT-5 | " | 26.5 | 29.2 |
| 58 | TPT-6 | " | 27.2 | 28.4 |
| 59 | TPT-7 | " | 30.1 | 32.2 |
| 60 | TPT-8 | " | 32.8 | 33.1 |
| 61 | TPT-9 | " | 29.2 | 31.5 |
| 62 | TPT-10 | " | 36.3 | 37.8 |
| 63 | TPT-11 | " | 35.7 | 38.2 |
| 64 | TPT-12 | " | 35.2 | 41.0 |
| 65 | TPT-13 | " | 39.5 | 42.1 |
| 66 | TPT-14 | " | 37.3 | 40.6 |
| 67 | MPM-1 | " | 21.1 | 21.9 |
| 68 | MPM-2 | " | 21.2 | 20.3 |
| 69 | MPM-3 | " | 25.4 | 27.1 |
| 70 | MPM-4 | " | 27.2 | 31.4 |
| 71 | MPM-5 | " | 32.4 | 32.7 |
| 72 | MPM-6 | " | 33.7 | 35.2 |
| 73 | HPH-1 | " | 22.2 | 22.5 |
| 74 | HPH-2 | " | 25.8 | 26.3 |
| 75 | HPH-3 | " | 31.2 | 31.2 |
| 76 | HPH-4 | " | 29.0 | 29.2 |
| 77 | HPH-5 | " | 29.2 | 30.4 |
| 78 | HPH-6 | " | 34.3 | 35.1 |

TABLE 15

| Example No. | Adhesive components Urethane prepolymer contg. two terminal isocyanate groups | Radical-polymerizabe unsat. monomer/visible light poly. initiator mixture | Bond strength to dentin (kg/cm²) After storage in water at 37° C. for 1 day | for 7 days |
|---|---|---|---|---|
| 79 | TPT-1 | LC-23 | 22.1 | 26.5 |
| 80 | TPT-2 | " | 21.3 | 26.1 |
| 81 | TPT-3 | " | 22.0 | 25.2 |
| 82 | TPT-4 | " | 24.5 | 29.9 |
| 83 | TPT-5 | " | 26.1 | 31.6 |
| 84 | TPT-6 | " | 27.0 | 38.6 |
| 85 | TPT-7 | " | 28.1 | 37.5 |
| 86 | TPT-8 | " | 30.9 | 40.0 |
| 87 | TPT-9 | " | 30.1 | 37.0 |
| 88 | TPT-10 | " | 36.4 | 30.8 |
| 89 | TPT-11 | " | 21.6 | 33.7 |
| 90 | TPT-12 | " | 28.2 | 18.8 |
| 91 | TPT-13 | " | 27.4 | 24.6 |
| 92 | TPT-14 | " | 23.7 | 30.8 |
| 93 | MPM-1 | " | 18.8 | 29.1 |
| 94 | MPM-2 | " | 27.0 | 24.8 |
| 95 | MPM-3 | " | 22.4 | 26.7 |
| 96 | MPM-4 | " | 33.7 | 25.5 |
| 97 | MPM-5 | " | 33.1 | 29.2 |
| 98 | MPM-6 | " | 31.5 | 33.8 |
| 99 | HPH-1 | " | 22.4 | 26.4 |
| 100 | HPH-2 | " | 30.3 | 35.9 |
| 101 | HPH-3 | " | 29.1 | 19.8 |
| 102 | HPH-4 | " | 27.5 | 26.4 |
| 103 | HPH-5 | " | 24.8 | 26.6 |
| 104 | HPH-6 | " | 30.9 | 31.9 |

TABLE 16

| Example No. | Adhesive components Urethane prepolymer contg. two terminal isocyanate groups | Radical-polymerizabe unsat. monomer/visible light poly. initiator mixture | Bond strength to dentin (kg/cm²) After storage in water at 37° C. for 1 day | for 7 days |
|---|---|---|---|---|
| 105 | TS-1 | LC-56 | 30.4 | 28.8 |
| 106 | TS-2 | " | 26.3 | 26.0 |
| 107 | MS-1 | " | 29.4 | 28.0 |
| 108 | MS-2 | " | 33.7 | 30.4 |
| 109 | MS-3 | " | 28.2 | 30.7 |
| 110 | MS-4 | " | 24.9 | 25.5 |
| 111 | MS-5 | " | 25.2 | 22.9 |
| 112 | MS-6 | " | 23.6 | 24.4 |
| 113 | HS-1 | " | 26.2 | 24.6 |
| 114 | HS-2 | " | 25.7 | 25.9 |
| 115 | TS-1 | LC-57 | 29.8 | 30.2 |

TABLE 16-continued

| Example No. | Adhesive components Urethane prepolymer contg. two terminal isocyanate groups | Radical-polymerizabe unsat. monomer/visible light poly. initiator mixture | Bond strength to dentin (kg/cm²) After storage in water at 37° C. for 1 day | for 7 days |
|---|---|---|---|---|
| 116 | TS-2 | " | 27.6 | 28.2 |
| 117 | MS-1 | " | 27.7 | 26.9 |
| 118 | MS-2 | " | 32.0 | 29.8 |
| 119 | MS-3 | " | 28.8 | 29.0 |
| 120 | MS-4 | " | 27.0 | 26.1 |
| 121 | MS-5 | " | 25.5 | 26.4 |
| 122 | MS-6 | " | 25.7 | 23.9 |
| 123 | HS-1 | " | 26.6 | 27.4 |
| 124 | HS-2 | " | 25.3 | 24.1 |

EXAMPLES 125 TO 130

A series of adhesive compositions were prepared by mixing various urethane prepolymers containing three free isocyanate groups, which had been obtained in the foregoing synthesis of urethane prepolymers (VII), with the radical-polymerizable unsaturated monomer/visible light polymerization initiator mixture LC-56 or LC-57 in a weight ratio of 1:1.

According to the above-described procedure for the evaluation of adhesivity and the above-described method for the measurement of bond strength, each of these adhesive compositions was used to bond restorative material A to an unetched dentin surface and an etched enamel surface, and the resulting bond strengths were measured. The results thus obtained are shown in Table 17.

TABLE 17

| Example No. | Adhesive components Urethane prepolymer contg. three free isocyanate groups | Radical-polymeriazbe unsat. monomer/visibe light poly. initiator mixture | Bond strength to dentin (kg/cm²) After being stored in water at 37° C. for 1 day | for 7 days | Bond strength to enamel (kg/cm²) After being stored in water at 37° C. for 1 day | for 7 days |
|---|---|---|---|---|---|---|
| 125 | CO-1 | LC-56 | 27.8 | 28.3 | 176 | 152 |
| 126 | CO-2 | " | 28.6 | 26.2 | 153 | 168 |
| 127 | CO-3 | " | 24.5 | 26.9 | 160 | 133 |
| 128 | CO-4 | LC-57 | 31.6 | 28.4 | 145 | 161 |
| 129 | CO-5 | " | 29.1 | 30.2 | 184 | 157 |
| 130 | CO-6 | " | 26.4 | 29.2 | 163 | 142 |

EXAMPLES 131 TO 203

Several series of adhesive compositions were prepared by mixing the isocyanate-containing urethane prepolymer TPT-11, MS-2 or CO-2, which had been obtained in the foregoing synthesis of urethane prepolymers (I), (V) or (VII), with various radical-polymerizable unsaturated monomer/visible light polymerization initiator mixtures in a weight ratio of 1:1.

Then, using restorative material A, the adhesivity of these adhesive compositions was evaluated in the same manner as described in Example 1. The results thus obtained are shown in Tables 18 to 21.

TABLE 18

| Example No. | Adhesive components Urethane prepolymer contg. two terminal isocyanate groups | Radical-polymerizable unsat. monomer/visible light poly. initiator mixture | Bond strength to dentin (kg/cm²) After storage in water at 37° C. for 1 day |
|---|---|---|---|
| 131 | TPT-11 | LC-1 | 13.0 |
| 132 | " | LC-2 | 12.1 |
| 133 | " | LC-3 | 28.6 |
| 134 | " | LC-4 | 29.0 |
| 135 | " | LC-5 | 20.0 |
| 136 | " | LC-6 | 23.0 |
| 137 | " | LC-7 | 26.6 |
| 138 | " | LC-8 | 23.2 |
| 139 | " | LC-9 | 20.2 |
| 140 | " | LC-10 | 20.0 |
| 141 | " | LC-11 | 15.7 |
| 142 | " | LC-12 | 16.8 |
| 143 | " | LC-13 | 19.6 |
| 144 | " | LC-14 | 28.2 |
| 145 | " | LC-17 | 33.0 |
| 146 | " | LC-18 | 34.8 |
| 147 | " | LC-19 | 37.9 |

TABLE 19

| Example No. | Adhesive components Urethane prepolymer contg. two terminal isocyanate groups | Radical-polymerizable unsat. monomer/visible light poly. initiator mixture | Bond strength to dentin (kg/cm$^2$) After storage in water at 37° C. for 1 day |
|---|---|---|---|
| 148 | TPT-11 | LC-20 | 26.9 |
| 149 | " | LC-21 | 27.8 |
| 150 | " | LC-22 | 32.4 |
| 151 | " | LC-23 | 33.7 |
| 152 | " | LC-24 | 25.5 |
| 153 | " | LC-25 | 26.1 |
| 154 | " | LC-26 | 38.8 |
| 155 | " | LC-27 | 38.6 |
| 156 | " | LC-28 | 35.4 |
| 157 | " | LC-29 | 37.1 |
| 158 | " | LC-30 | 21.9 |
| 159 | " | LC-31 | 24.7 |
| 160 | " | LC-32 | 28.6 |
| 161 | " | LC-33 | 29.3 |
| 162 | " | LC-34 | 41.8 |
| 163 | " | LC-35 | 43.2 |

TABLE 20

| Example No. | Adhesive components Urethane prepolymer contg. two terminal isocyanate groups | Radical-polymerizable unsat. monomer/visible light poly. initiator mixture | Bond strength to dentin (kg/cm$^2$) After storage in water at 37° C. for 1 day |
|---|---|---|---|
| 164 | MS-2 | LC-36 | 18.2 |
| 165 | " | LC-37 | 16.9 |
| 166 | " | LC-38 | 26.6 |
| 167 | " | LC-39 | 22.4 |
| 168 | " | LC-40 | 29.8 |
| 169 | " | LC-41 | 28.0 |
| 170 | " | LC-42 | 30.4 |
| 171 | " | LC-43 | 33.2 |
| 172 | " | LC-44 | 29.1 |
| 173 | " | LC-45 | 27.5 |
| 174 | " | LC-46 | 25.5 |
| 175 | " | LC-47 | 26.9 |
| 176 | " | LC-48 | 30.1 |
| 177 | " | LC-51 | 28.2 |
| 178 | " | LC-52 | 34.0 |
| 179 | " | LC-53 | 32.8 |
| 180 | " | LC-54 | 30.4 |

TABLE 21

| Example No. | Adhesive components Urethane prepolymer contg. two terminal isocyanate groups | Radical-polymerizable unsat. monomer/visible light poly. initiator mixture | Bond strength to dentin (kg/cm$^2$) After storage in water at 37° C. for 1 day |
|---|---|---|---|
| 181 | CO-2 | LC-36 | 18.2 |
| 182 | " | LC-37 | 16.6 |
| 183 | " | LC-38 | 27.4 |
| 184 | " | LC-39 | 22.5 |
| 185 | " | LC-40 | 33.0 |
| 186 | " | LC-41 | 28.4 |
| 187 | " | LC-42 | 29.3 |
| 188 | " | LC-43 | 28.2 |
| 189 | " | LC-44 | 24.1 |
| 190 | " | LC-45 | 25.0 |
| 191 | " | LC-46 | 27.8 |
| 192 | " | LC-47 | 28.2 |
| 193 | " | LC-48 | 26.7 |
| 194 | " | LC-51 | 29.4 |
| 195 | " | LC-52 | 35.4 |
| 196 | " | LC-53 | 30.1 |
| 197 | " | LC-54 | 34.5 |
| 198 | " | LC-55 | 26.3 |
| 199 | " | LC-56 | 32.5 |
| 200 | " | LC-57 | 28.8 |
| 201 | " | LC-58 | 27.3 |
| 202 | " | LC-59 | 29.0 |
| 203 | " | LC-60 | 31.6 |

EXAMPLES 204 TO 228

According to the same procedure as described in Example 1, several series of adhesive compositions were prepared by using various urethane prepolymers containing one terminal isocyanate group and one terminal hydroxyl group, which had been obtained in the foregoing synthesis of urethane prepolymers (II), (III) or (VI), and various urethane prepolymers containing one terminal radical-polymerizable vinyl group and one terminal isocyanate group, which had been obtained in the foregoing synthesis of urethane prepolymers (III). Then, the adhesivity of these adhesive compositions was evaluated in the same manner as described in Example 1. The results thus obtained are shown in Tables 22 and 23.

EXAMPLES 229 TO 234

According to the same procedure as described in Example 128, a series of adhesive compositions were prepared by using various urethane prepolymers containing one radical-polymerizable vinyl group and two free isocyanate groups and various urethane prepolymers containing two radical-polymerizable vinyl groups and one free isocyanate group, which had been obtained in the foregoing synthesis of urethane prepolymers (VIII). Then, the adhesivity of these adhesive compositions was evaluated in the same manner as described in Example 1. The results thus obtained are shown in Table 24.

TABLE 22

| Example No. | Adhesive components — Urethane prepolymer contg. one terminal isocyanate group and one terminal hydroxyl group | Radical-polymerizable unsat. monomer/visible light poly. initiator mixture | Bond strength to dentin (kg/cm$^2$) After storage in 37° C. for 1 day |
|---|---|---|---|
| 204 | PT-1 | LC-15 | 12.0 |
| 205 | PT-2 | " | 10.0 |
| 206 | PT-3 | " | 10.2 |
| 207 | PT-4 | " | 13.1 |
| 208 | PT-5 | " | 12.4 |
| 209 | PT-6 | " | 12.0 |
| 210 | PM-1 | " | 8.7 |
| 211 | PM-2 | " | 9.8 |
| 212 | PM-3 | " | 10.3 |
| 213 | PH-1 | " | 10.0 |
| 214 | PH-2 | " | 11.8 |
| 215 | PH-3 | " | 14.1 |
|  | Urethane prepolymer contg. one terminal radical-polymerizable vinyl group and one terminal isocyanate group |  |  |
| 216 | TV-1 | LC-15 | 18.0 |
| 217 | TV-2 | " | 16.7 |
| 218 | TV-3 | " | 17.0 |
| 219 | MV-1 | " | 13.8 |
| 220 | HV-1 | " | 15.0 |

TABLE 23

| Example No. | Adhesive components — Urethane prepolymer contg. one terminal isocyanate group and one terminal hydroxyl group | Radical-polymerizable unsat. monomer/visible light poly. initiator mixture | Bond strength to dentin (kg/cm$^2$) After storage in 32° C. for 1 day |
|---|---|---|---|
| 221 | TH-1 | LC-56 | 10.4 |
| 222 | PT-2 | " | 8.9 |
| 223 | MH-1 | " | 13.3 |
| 224 | PT-2 | " | 10.9 |
| 225 | PT-3 | " | 11.2 |
| 226 | PT-4 | " | 8.0 |
| 227 | PM-1 | " | 10.4 |
| 228 | PM-2 | " | 7.7 |

TABLE 24

| Example No. | Adhesive components — Urethane prepolymer contg. one (two) radical polymerizable unsat. two (one) free isocyanate groups | Radical-polymerizable unsat. monomer/visible light poly. initiator mixture | Bond strength to dentin (kg/cm$^2$) After storage in 37° C. for 1 day |
|---|---|---|---|
| 229 | SV-1 | LC-56 | 23.2 |
| 230 | SV-2 | " | 27.0 |
| 231 | SV-3 | " | 24.9 |
| 232 | VV-1 | " | 16.8 |
| 233 | VV-2 | " | 13.4 |
| 234 | VV-3 | " | 15.7 |

EXAMPLES 235 TO 246

According to the same procedure as described in Examples 7, 33, 59 or 85, various adhesive compositions were prepared by varying the weight ratio of the urethane prepolymer containing two terminal isocyanate groups to the radical-polymerizable unsaturated monomer/visible light polymerization initiator mixture. Then, the bonding power of these adhesive compositions was evaluated in the same manner as described in Example 1. The results thus obtained are shown in Table 25.

TABLE 25

| | Ratio between adhesive components (parts by weight) | | Bond strength to dentin (kg/cm$^2$) |
|---|---|---|---|
| Example No. | Urethane prepolymer contg. two terminal isocyanate groups | Radical-polymerizable unsat. monomer/visible light poly. initiator mixture | After storage in water at 37° C. for 1 day |
| 235 | TPT-7:10 | LC-15:90 | 20.0 |
| 236 | TPT-7:30 | LC-15:70 | 24.0 |
| 237 | TPT-7:80 | LC-15:20 | 31.2 |
| 238 | TPT-7:10 | LC-16:90 | 20.0 |
| 239 | TPT-7:30 | LC-16:70 | 24.4 |
| 240 | TPT-7:80 | LC-16:20 | 35.0 |
| 241 | TPT-7:10 | LC-22:90 | 23.7 |
| 242 | TPT-7:30 | LC-22:70 | 28.6 |
| 243 | TPT-7:80 | LC-22:20 | 35.2 |
| 244 | TPT-7:10 | LC-23:90 | 21.9 |
| 245 | TPT-7:30 | LC-23:70 | 23.0 |
| 246 | TPT-7:80 | LC-23:20 | 36.2 |

EXAMPLES 247 TO 249

According to the same procedure as described in Example 125, various adhesive compositions were prepared by varying the weight ratio of the urethane prepolymer containing three free isocyanate groups to the radical-polymerizable unsaturate monomer/visible light polymerization initiator mixture. Then, the adhesivity of these adhesive compositions to an unetched dentin surface was evaluated in the same manner as described in Example 1. The results thus obtained are shown in Table 26.

TABLE 26

| | Ratio between adhesive components (parts by weight) | | Bond strength to dentin (kg/cm$^2$) |
|---|---|---|---|
| Example No. | Urethane prepolymer contg. three free isocyanate groups | Radical-polymerizable unsat. monomer/visible light poly. initiator mixture | After storage in water at 37° C. for 1 day |
| 247 | CO-1:10 | LC-56:90 | 14.1 |
| 248 | CO-1:30 | LC-56:70 | 22.4 |
| 249 | CO-1:80 | LC-56:20 | 31.0 |

EXAMPLES 250 TO 265

Using the adhesive compositions obtained in Examples 10, 62, 118 and 129, their adhesivity to various restorative materials was evaluated in the same manner as described in Example 1. The results thus obtained are shown in Table 27.

TABLE 27

| Example No. | Adhesive composition | Type of restorative material | Bond strength to dentin (kg/cm$^2$) *1 |
|---|---|---|---|
| 250 | Example 10 | Restorative material B | 38.2 |
| 251 | " | Commercially available one-paste composite resin *2 | 35.0 |
| 252 | " | Commercially available two-paste composite resin *3 | 29.6 |
| 253 | " | Polymethyl methacrylate *4 | 31.0 |
| 254 | Example 62 | Restorative material B | 34.7 |
| 255 | " | Commercially available one-paste composite resin *2 | 29.4 |
| 256 | " | Commercially available two-paste composite resin *3 | 31.5 |
| 257 | " | Polymethyl methacrylate *4 | 30.5 |
| 258 | Example 117 | Restorative material B | 32.9 |
| 259 | " | Commercially available one-paste composite resin *2 | 26.4 |
| 260 | " | Commercially available two-paste composite resin *3 | 28.8 |
| 261 | " | Polymethyl methacrylate *4 | 25.1 |
| 262 | Example 129 | Restorative material B | 30.8 |
| 263 | " | Commercially available one-paste composite resin *2 | 24.6 |
| 264 | " | Commercially available two-paste composite resin *3 | 28.5 |
| 265 | " | Polymethyl methacrylate *4 | 29.0 |

*1: Measured after storage in water at 37° C. for 1 day.
*2: Occlusin (trade name; a product of ICI Co.).
*3: Microrest AP (trade name; a product of GC Dental Industries Co.).
*4: Acrypet #VH (trade name; a product of Mitsubishi Rayon Co., Ltd.).

COMPARATIVE EXAMPLES 1 TO 14

According to the same procedure as described in Example 1, a series of adhesive compositions were prepared by using various polyether glycols, which had been obtained in the foregoing synthesis of urethane prepolymers (I), in place of the urethane prepolymer containing two terminal isocyanate groups. Then, the bonding power of these adhesive compositions was evaluated in the same manner as described in Example 1. The results thus obtained are shown in Table 28.

TABLE 28

| Comparative Example No. | Adhesive components | | Bond strength to dentin (kg/cm$^2$) After storage in water at 37° C. 1 day |
|---|---|---|---|
| | Polyether glycol | Radical-polymerizable unsat. monomer/visible light poly. initiator mixture | |
| 1 | PEP-1 | LC-15 | 0.0 |
| 2 | PEP-2 | " | 0.0 |
| 3 | PEP-3 | " | 0.0 |
| 4 | PEP-4 | " | 0.0 |
| 5 | PEP-5 | " | 0.0 |
| 6 | PEP-6 | " | 0.0 |
| 7 | PEP-7 | " | 0.0 |
| 8 | PEP-8 | " | 0.0 |
| 9 | PEP-9 | " | 0.0 |
| 10 | PEP-10 | " | 0.0 |
| 11 | PEP-11 | " | 0.0 |
| 12 | PEP-12 | " | 0.0 |
| 13 | PEP-13 | " | 0.0 |
| 14 | PEP-14 | " | 0.0 |

COMPARATIVE EXAMPLES 15 TO 20

According to the same procedure as described in Example 1, a series of adhesive compositions were prepared by using various polyester glycols, which had been obtained in the foregoing synthesis of urethane prepolymers (V), in place of the urethane prepolymer containing two terminal isocyanate groups. Then, the bonding power of these adhesive compositions was evaluated in the same manner as described in Example 1. The results thus obtained are shown in Table 29.

TABLE 29

| Comp. Example No. | Adhesive components | | Bond strength to dentin (kg/cm$^2$) After storage in water at 37° C. 1 day |
|---|---|---|---|
| | Polyether glycol | Radical-polymerizable unsat. monomer/visible light poly. initiator mixture | |
| 15 | SG-1 | LC-57 | 0.0 |
| 16 | SG-2 | " | 0.0 |
| 17 | SG-3 | " | 0.0 |
| 18 | SG-4 | " | 0.0 |
| 19 | SG-5 | " | 0.0 |
| 20 | SG-6 | " | 0.0 |

COMPARATIVE EXAMPLE 21 TO 23

According to the same procedure as described in Example 125, a series of adhesive compositions were prepared by using various urethane prepolymers having two terminal radical-polymerizable vinyl groups, which had been obtained in the foregoing synthesis of urethane prepolymers (IX), in place of the urethane prepolymer containing two terminal isocyanate groups. Then, the adhesivity of these adhesive compositions was evaluated in the same manner as described in Example 1. The results thus obtained are shown in Table 30.

TABLE 30

| Comp. Example No. | Adhesive components | | Bond strength to dentin (kg/cm$^2$) After storage in water at 37° C. for 1 day |
|---|---|---|---|
| | Urethane prepolymer contg. two terminal radical-polymerizable vinyl groups | Radical-polymerizable unsat. monomer/visible light poly. initiator mixture | |
| 21 | DV-1 | LC-15 | 0.0 |
| 22 | DV-2 | " | 0.0 |
| 23 | DV-3 | " | 0.0 |

COMPARATIVE EXAMPLES 24 TO 29

According to the same procedure as described in Example 125 or 128, a series of adhesive compositions were prepared by using various urethane prepolymers having three radical-polymerizable vinyl groups, which has been obtained in the foregoing synthesis of urethane prepolymers (IX), in place of the urethane prepolymer containing three free isocyanate groups. Then, the adhesivity of these adhesive compositions was evaluated in the same manner as described in Example 1. The results thus obtained are shown in Table 31.

TABLE 31

| Comp. Example No. | Adhesive components | | Bond strength to dentin (kg/cm$^2$) After storage in water at 37° C. for 1 day |
|---|---|---|---|
| | Urethane prepolymer contg. three radical-polymerizable vinyl groups | Radical-polymerizable unsat. monomer/visible light poly. initiator mixture | |
| 24 | PV-1 | LC-56 | 0.0 |
| 25 | PV-2 | " | 0.0 |
| 26 | PV-3 | " | 0.0 |
| 27 | PV-1 | LC-57 | 0.0 |
| 28 | PV-2 | " | 0.0 |
| 29 | PV-3 | " | 0.0 |

EXAMPLES 266 TO 317

A series of adhesive compositions were prepared by mixing various urethane prepolymers containing two terminal isocyanate groups, which had been obtained in the foregoing synthesis of urethane prepolymers (I), with the monomer X/monomer Z/visible light polymerization initiator mixture LC-69 in a weight ratio of 1:1.

According to the above-described procedure for the evaluation of adhesivity and the above-described method for the measurement of bond strength, each of these adhesive compositions was used to bond restorative material A to an unetched dentin surface of a cattle tooth, and the resulting bond strength was measured. The results thus obtained are shown in Table 32.

Moreover, another series of adhesive compositions were prepared with LC-64 and evaluated in the same manner. The results thus obtained are also shown in Table 32.

TABLE 32

| Example No. | Adhesive components - Urethane prepolymer contg. two terminal isocyanate groups | Monomer X/monomer Z/visible light poly. initiator mixture | Bond strength to dentin (kg/cm$^2$) After storage in water at 37° C. for 1 day | for 7 days |
|---|---|---|---|---|
| 266 | TPT-1 | LC-69 | 37.1 | 37.8 |
| 267 | TPT-2 | " | 38.7 | 35.4 |
| 268 | TPT-3 | " | 38.0 | 40.9 |
| 269 | TPT-4 | " | 39.5 | 38.8 |
| 270 | TPT-5 | " | 37.8 | 37.9 |
| 271 | TPT-6 | " | 39.8 | 39.7 |
| 272 | PTP-7 | " | 42.2 | 42.0 |
| 273 | TPT-8 | " | 43.7 | 45.0 |
| 274 | TPT-9 | " | 41.5 | 41.8 |
| 275 | TPT-10 | " | 48.8 | 47.7 |
| 276 | TPT-11 | " | 47.4 | 47.6 |
| 277 | TPT-12 | " | 45.2 | 44.8 |
| 278 | TPT-13 | " | 50.9 | 47.8 |
| 279 | TPT-14 | " | 59.5 | 51.1 |
| 280 | MPM-1 | " | 33.0 | 34.2 |
| 281 | MPM-2 | " | 33.7 | 33.5 |
| 282 | MPM-3 | " | 37.6 | 39.2 |
| 283 | MPM-4 | " | 43.5 | 45.1 |
| 284 | MPM-5 | " | 45.5 | 46.4 |
| 285 | MPM-6 | " | 34.2 | 33.9 |
| 286 | HPH-1 | " | 37.7 | 35.4 |
| 287 | HPH-2 | " | 42.8 | 42.9 |
| 288 | HPH-3 | " | 41.0 | 41.7 |
| 289 | HPH-4 | " | 40.6 | 42.5 |
| 290 | HPH-5 | " | 41.2 | 40.7 |
| 291 | HPH-6 | " | 46.3 | 47.5 |
| 292 | TPT-1 | LC-64 | 39.7 | 38.2 |
| 293 | TPT-2 | " | 35.2 | 42.5 |
| 294 | TPT-3 | " | 35.7 | 39.5 |
| 295 | TPT-4 | " | 37.7 | 36.3 |
| 296 | TPT-5 | " | 39.6 | 38.7 |
| 297 | TPT-6 | " | 43.6 | 42.6 |
| 298 | TPT-7 | " | 41.4 | 51.9 |
| 299 | TPT-8 | " | 45.1 | 45.7 |
| 300 | TPT-9 | " | 43.4 | 43.0 |
| 301 | TPT-10 | " | 47.7 | 47.9 |
| 302 | TPT-11 | " | 49.0 | 47.8 |
| 303 | TPT-12 | " | 51.4 | 50.0 |
| 304 | TPT-13 | " | 45.2 | 49.4 |
| 305 | TPT-14 | " | 51.4 | 52.5 |
| 306 | MPM-1 | " | 35.5 | 32.5 |
| 307 | MPM-2 | " | 35.6 | 30.7 |
| 308 | MPM-3 | " | 38.7 | 38.8 |
| 309 | MPM-4 | " | 44.2 | 43.2 |
| 310 | MPM-5 | " | 45.5 | 46.0 |
| 311 | MPM-6 | " | 47.7 | 47.5 |
| 312 | HPH-1 | " | 36.4 | 35.4 |
| 313 | HPH-2 | " | 38.7 | 36.4 |
| 314 | HPH-3 | " | 43.1 | 43.4 |
| 315 | HPH-4 | " | 39.3 | 38.9 |
| 316 | HPH-5 | " | 43.9 | 43.1 |
| 317 | HPH-6 | " | 45.5 | 45.5 |

EXAMPLES 318 TO 327

A series of adhesive compositions were prepared by mixing the urethane prepolymer TPT-11 containing two terminal isocyanate groups, which had been obtained in the foregoing synthesis of urethane prepolymers (I), with various monomer X/monomer Z/visible light polymerization initiator mixtures in a weight ratio of 1:1.

Then, using restorative material A, the adhesivity of these adhesive compositions was evaluated in the same manner as described in Example 1. The results thus obtained are shown in Table 33.

TABLE 33

| Example No. | Adhesive Components - Urethane prepolymer contg. two terminal isocyanate groups | Monomer X/monomer Z/visible light poly. initiator mixture | Bond strength to dentin (kg/cm$^2$) After storage in water at 37° C. for 1 day |
|---|---|---|---|
| 318 | TPT-11 | LC-61 | 30.5 |
| 319 | " | LC-62 | 33.7 |
| 320 | " | LC-63 | 36.8 |
| 321 | " | LC-64 | 38.9 |
| 322 | " | LC-65 | 28.4 |
| 323 | " | LC-66 | 27.5 |
| 324 | " | LC-67 | 45.6 |
| 325 | " | LC-68 | 48.3 |
| 326 | " | LC-69 | 51.0 |

TABLE 33-continued

| Example No. | Adhesive Components | | Bond strength to dentin (kg/cm²) After storage in water at 37° C. for 1 day |
|---|---|---|---|
| | Urethane prepolymer contg. two terminal isocyanate groups | Monomer X/monomer Z/visible light poly. initiator mixture | |
| 327 | " | LC-70 | 50.1 |

EXAMPLES 328 TO 344

A series of adhesive compositions were prepared by mixing the urethane prepolymer TPT-11 containing two terminal isocyanate groups, which had been obtained in the foregoing synthesis of urethane prepolymers (I), with various monomer X/monomer Z/visible light polymerization initiator mixtures (i.e, LC-73 to LC-88) in a weight ratio of 1:1.

Then, using restorative material A, the adhesivity of these adhesive compositions was evaluated in the same manner as described in Example 1. The results thus obtained are shown in Table 34.

TABLE 34

| Example No. | Adhesive Components | | Bond strength to dentin (kg/cm²) After storage in water at 37° C. for 1 day |
|---|---|---|---|
| | Urethane prepolymer contg. two terminal isocyanate groups | Monomer X/monomer Z/visible light poly. initiator mixture | |
| 328 | TPT-11 | LC-73 | 35.4 |
| 329 | " | LC-74 | 33.0 |
| 330 | " | LC-75 | 43.8 |
| 331 | " | LC-76 | 40.5 |
| 332 | " | LC-77 | 49.7 |
| 333 | " | LC-78 | 48.6 |
| 334 | " | LC-79 | 37.5 |
| 335 | " | LC-80 | 37.1 |
| 336 | " | LC-81 | 29.9 |
| 337 | " | LC-82 | 32.2 |
| 338 | " | LC-83 | 36.8 |
| 339 | " | LC-84 | 41.1 |
| 340 | " | LC-85 | 35.2 |
| 341 | " | LC-86 | 37.9 |
| 342 | " | LC-87 | 47.5 |
| 343 | " | LC-89 | 46.3 |
| 344 | " | LC-89 | 46.8 |

COMPARATIVE EXAMPLES 30 TO 43

According to the same procedure as described in Example 1, a series of adhesive compositions were prepared by using various polyether glycols, which had been obtained in the foregoing synthesis of urethane prepolymers (I), in place of the urethane prepolymer containing two terminal isocyanate groups. Then, the adhesivity of these adhesive compositions was evaluated in the same manner as described in Example 1. The results thus obtained are shown in Table 35.

TABLE 35

| Comp. Example No. | Adhesive components | | Bond strength to dentin (kg/cm²) After storage in water at 37° C. for 1 day |
|---|---|---|---|
| | Polyether glycol | Monomer X/monomer Z/visible light poly. initiator mixture | |
| 30 | PEP-1 | LC-63 | 0.0 |
| 31 | PEP-2 | " | 0.0 |
| 32 | PEP-3 | " | 0.0 |
| 33 | PEP-4 | " | 0.0 |
| 34 | PEP-5 | " | 0.0 |
| 35 | PEP-6 | " | 0.0 |
| 36 | PEP-7 | " | 0.0 |
| 37 | PEP-8 | " | 0.0 |
| 38 | PEP-9 | " | 0.0 |
| 39 | PEP-10 | " | 0.0 |
| 40 | PEP-11 | " | 0.0 |
| 41 | PEP-12 | " | 0.0 |
| 42 | PEP-13 | " | 0.0 |
| 43 | PEP-14 | " | 0.0 |

COMPARATIVE EXAMPLES 44 TO 55

A series of adhesive compositions comprising various monomer X/monomer Z/visible light polymerization initiator mixture alone were prepared. Then, the adhesivity of these adhesive compositions was evaluated in the same manner as described in Example 1. The results thus obtained are shown in Table 36.

TABLE 36

| Comp. Example No. | Adhesive Components | | Bond strength to dentin (kg/cm²) After storage in water at 37° C. for 1 day |
|---|---|---|---|
| | Urethane prepolymer contg. two terminal isocyanate groups | Monomer X/monomer Z/visible light poly. initiator mixture | |
| 44 | Not used | LC-61 | 30.5 |
| 45 | " | LC-62 | 0.0 |
| 46 | " | LC-63 | 0.0 |
| 47 | " | LC-64 | 0.0 |
| 48 | " | LC-65 | 0.0 |
| 49 | " | LC-66 | 0.0 |
| 50 | " | LC-67 | 0.0 |
| 51 | " | LC-68 | 0.0 |
| 52 | " | LC-69 | 0.0 |
| 53 | " | LC-70 | 0.0 |
| 54 | " | LC-71 | 0.0 |
| 55 | " | LC-72 | 0.0 |

COMPARATIVE EXAMPLES 56 TO 59

A series of adhesive compositions were prepared by mixing the urethane prepolymer TPT-11 containing two terminal isocyanate groups, which had been obtained in the foregoing synthesis of urethane prepolymers (I), with various monomer X/monomer Z/visible light polymerization initiator mixtures as shown in Table 38 (i.e., LC-77, to LC-80), in a weight ratio of 1:1.

Then, using restorative material A, the adhesivity of these adhesive compositions was evaluated in the same manner as described in Example 1. The results thus obtained are shown in Table 37.

TABLE 37

| Comp. Example No. | Adhesive Components | | Bond strength to dentin (kg/cm²) After storage in water at 37° C. for 1 day |
|---|---|---|---|
| | Urethane prepolymer contg. two terminal isocyanate groups | Monomer X/monomer Z/visible light poly. initiator mixture | |
| 56 | TPT-11 | LC-90 | 15.3 |
| 57 | " | LC-91 | 17.1 |
| 58 | " | LC-92 | 11.8 |
| 59 | " | LC-93 | 9.0 |

TABLE 38

| Code for monomer X/monomer Z/visible light poly. initiator mixture | Monomer X, monomer Z and amounts used | | | | | | | | | |
|---|---|---|---|---|---|---|---|---|---|---|
| | Acryloxy pivalate | Benzyl methacrylate | 2-Hydroxyethyl methacrylate | Triethylene glycol dimethacrylate | Bis-BMA | Bis-MEPP | U-4HA | U-6HA | Methacryloxyethyl phosphate | Dimethacryloxyethyl phosphate |
| LC-90 | — | — | 30 | 10 | — | 30 | 30 | — | 40.0 | — |
| LC-91 | — | — | " | " | — | " | " | — | — | 40.0 |
| LC-92 | — | — | " | " | — | " | " | — | 60.0 | — |
| LC-93 | — | — | " | " | — | " | " | — | — | 60.0 |

| Code for monomer X/monomer Z/visible light poly. initiator mixture | Visible light poly. initiator and amount used (g) | | |
|---|---|---|---|
| | Camphorquinone | Isoamyl 4-(N,N-dimethylamino) benzoate | 4,4'-Bis-(dimethylamino)-benzophenone |
| LC-90 | 0.8 | 1.2 | — |
| LC-91 | " | " | — |
| LC-92 | " | — | 12 |
| LC-93 | " | — | " |

EXAMPLES 345 TO 350

According to the same procedures as described in Example 1, various adhesive compositions were prepared by varying the weight ratio of the urethane prepolymer containing two terminal isocyanate groups to the monomer X/monomer Z/visible light polymerization initiator mixture. Then, the adhesivity of these adhesive compositions was evaluated in the same manner as described in Example 1. The results thus obtained are shown in Table 39.

TABLE 39

| Example No. | Ratio between adhesive components (parts by weight) | | Bond strength to dentin (kg/cm²) After storage in water at 37° C. for 1 day |
|---|---|---|---|
| | Urethane prepolymer contg. two terminal isocyanate groups | Monomer X/monomer Z/visible light poly. initiator mixture | |
| 345 | TPT-7:10 | LC-67:90 | 34.8 |
| 346 | :30 | :70 | 41.6 |
| 347 | :80 | :20 | 47.4 |
| 348 | :10 | LC-68:90 | 30.5 |
| 349 | :30 | :70 | 43.3 |
| 350 | :80 | :20 | 48.4 |

EXAMPLES 351 TO 354

Using the adhesive composition obtained in Example 275, its adhesivity to various restorative materials was evaluated in the same manner as described in Example 1. The results thus obtained are shown in Table 40.

TABLE 40

| Example No. | Restorative material | Bond strength to dentin (kg/cm²) *1 |
|---|---|---|
| 351 | Restorative material B | 40.5 |
| 352 | Commercially available one-paste composite resin *2 | 38.9 |
| 353 | Commercially available two-paste composite resin *3 | 33.7 |
| 354 | Polymethyl methacrylate *4 | 35.7 |

*1: Measured after storage in water at 37° C. for 1 day.
*2: Occlusin (trade name; a product of ICI Co.).
*3: Microrest AP (trade name; a product of GC Dental Industries Co.).
*4: Acrypet #VH (trade name; a product of Mitsubishi Rayon Co., Ltd.).

What is claimed is:

1. A dental adhesive composition consisting essentially of
   (a) at least one urethane prepolymer containing one or more isocyanate groups; or a blend of the urethane prepolymer and an inert diluent, where said urethane prepolymer contains isocyanate groups at each end;
   (b) At least one radical polymerizable unsaturated monomer;
   (c) a photopolymerization initiator; and
   (d) a polymerizable phosphoric ester compound of the general formula (1):

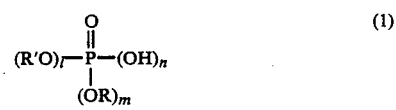

where R is a group selected from the class consisting of

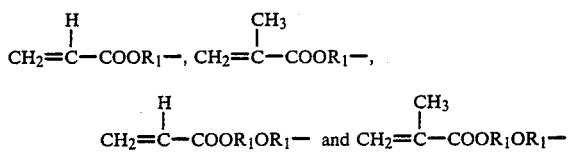

in which $R_1$ is an alkylene group, $R'$ is an alkyl group, n is 1 or 2, m is 1 or 2, l is 0 or 2 and the sum of (n+m+l) is equal to 3.

2. A dental adhesive composition as claimed in claim 1 wherein the urethane prepolymer containing one or more isocyanate groups is a compound of the structural formula (2):

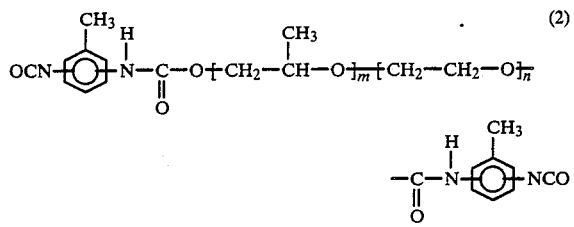

where m is a whole number of 1 to 100, n is a whole number of 0 to 100, and the propylene oxide units may be randomly joined to the ethylene oxide units.

3. A dental adhesive composition as claimed in claim 1 wherein the urethane prepolymer containing one or more isocyanate groups is a compound of the structural formula (3):

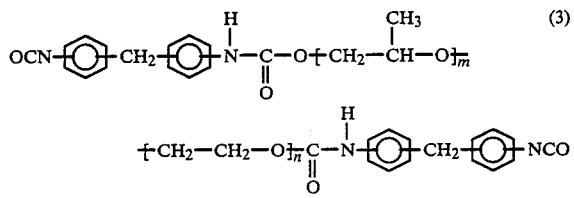

where m is a whole number of 1 to 100, n is a whole number of 0 to 100, and the propylene oxide units may be randomly joined to the ethylene oxide units.

4. A dental adhesive composition as claimed in claim 1 wherein the urethane prepolymer containing one or more isocyanate groups is a compound of the structural formula (4):

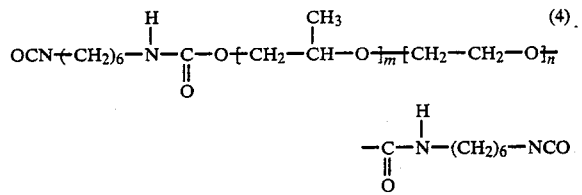

where m is a whole number of 1 to 100, n is a whole number of 0 to 100, and the propylene oxide units may be randomly joined to the ethylene oxide units.

5. A dental adhesive composition as claimed in claim 1 wherein the urethane prepolymer containing one or more isocyanate groups has an average molecular weight of 400 to 20,000.

6. A dental adhesive composition as claimed in claim 2 wherein the urethane prepolymer containing one or more isocyanate groups has been rendered hydrophilic or water-soluble by adjusting its ethylene oxide unit content to a level of 40 to 80 mole percent based on the combined amount of the propylene oxide units and ethylene oxide units constituting the prepolymer chain.

7. A dental adhesive composition as claimed in claim 1 wherein the urethane prepolymer containing one or more isocyanate groups is a compound obtained by reacting a polyester polyol with a polyisocyanate, the polyester polyol having the structural formula (5):

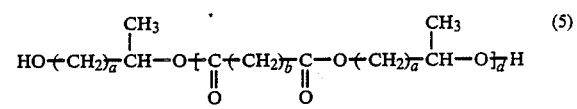

where a is a whole number of 1 to 5, b is a whole number of 4 to 10, and d is a whole number of 1 to 200.

8. A dental adhesive composition as claimed in claim 1 wherein the urethane prepolymer containing one or more isocyanate groups is a compound obtained by reacting castor oil or a derivative there of with a polyisocyanate.

9. A dental adhesive composition as claimed in claim 7 wherein the polyisocyanate is one or more compound selected from the group consisting of tolylene diisocyanate, 4,4'-diphenylmethane diisocyanate and hexamethylene diisocyanate.

10. A dental adhesive composition as claimed in claim 1 wherein the radical-polymerizable unsaturated monomer is a polyethylene glycol di(meth)acrylate of the general formula (7):

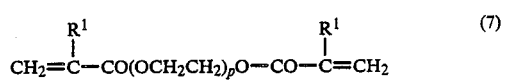

where $R^1$ is a hydrogen atom or a methyl group, and p is a whole number of 1 to 20.

11. A dental adhesive composition as claimed in claim 1 wherein the radical-polymerizable unsaturated monomer is a urethane di(meth)acrylate of the general formula (8):

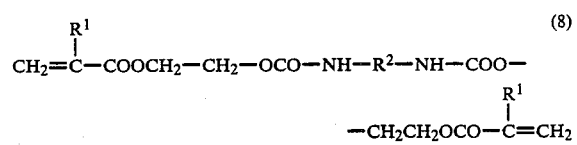

where $R^1$ is a hydrogen atom or a methyl group, and $R^2$ is an alkylene group of 1 to 8 carbon atoms, or

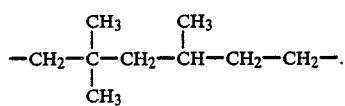

12. A dental adhesive composition as claimed in claim 1 wherein the radical-polymerizable unsaturated monomer is methyl acrylate, methyl methacrylate, vinyl acetate, ethylene glycol dimethacrylate, triethylene glycol dimethacrylate, triethylene glycol diacrylate, nonaethylene glycol diacrylate, nonaethylene glycol dimethacrylate, tetradecaethylene glycol dimethacrylate, tetradecaethylene glycol diacrylate, trimethylolpropane trimethacrylate, or the urethane dimethacrylate of the structural formula (9):

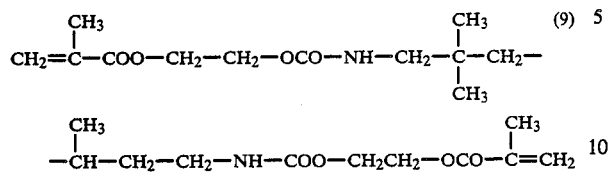

13. A dental adhesive composition as claimed in claim 1 wherein the radical-polymerizable unsaturated monomer is a (meth)acrylate compound having a bisphenol A skeleton and represented by the general formula (10) or (11):

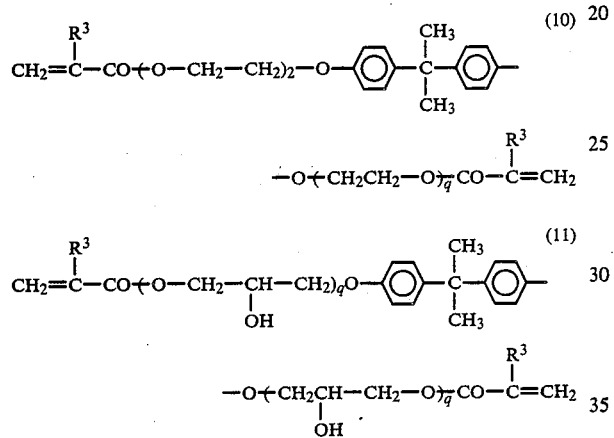

where $R^3$ is a hydrogen atom or a methyl group, and q is a whole number of 1 to 20.

14. A dental adhesive composition as claimed in claim 1 wherein the radical-polymerizable unsaturated monomer is a compound of the general formula (12):

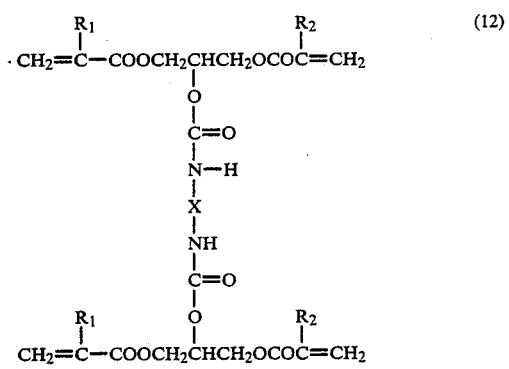

where $R_1$ and $R_2$ are hydrogen atoms or methyl groups, and X is $-CH_2-$, $-CH_2CH_2-$, $-(CH_2)_3-$, $-(CH_2)_4-$, $-(CH_2)_5-$, $-(CH_2)_6-$ or

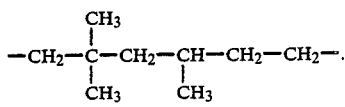

15. A dental adhesive composition as claimed in claim 1 wherein the radical-polymerizable unsaturated monomer is a hexafunctional urethane (meth)acrylate compound having an isocyanuric acid skeleton and represented by the general formula (13):

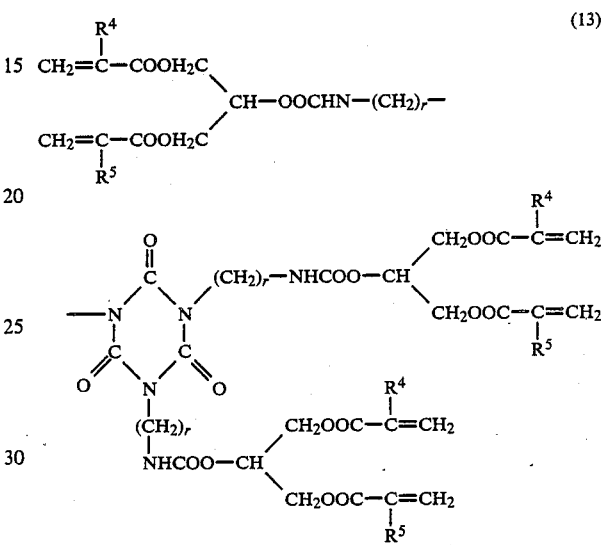

where $R^4$ and $R^5$ are hydrogen atoms or methyl groups, and r is a whole number of 1 to 10.

16. A dental adhesive composition as claimed in claim 1 wherein the photopolymerization initiator is a mixture of camphorquinone and isoamyl 4-(N,N-dimethylamino)benzoate.

17. A dental adhesive composition as claimed in claim 1 wherein the photopolymerization initiator is a mixture of camphorquinone and 4,4'-bis(dimethylamino)-benzophenone or 4,4'-bis(diethylamino)benzophenone.

18. A dental adhesive composition as claimed in claim 16 wherein the amounts of camphorquinone and isoamyl 4-(N,N-dimethylamino)benzoate used are 0.05 to 15% by weight and 0.1 to 25% by weight, respectively, based on the radical-polymerizable unsaturated monomer.

19. A dental adhesive composition as claimed in claim 1 wherein the amounts of camphorquinone and 4,4'-bis(dimethylamino)benzophenone used are 0.03 to 20% by weight and 0.05 to 20% by weight, respectively, based on the radical-polymerizable unsaturated monomer.

20. A dental adhesive composition as claimed in claim 1 wherein the weight ratio of component (a) to component (b) ranges from 1:50 to 50:1.

21. A dental adhesive composition as claimed in claim 1 wherein composition (a) and a blend of components (b) and (c) are stored separately and mixed just before use.

* * * * *